(12) United States Patent
Davenport et al.

(10) Patent No.: US 10,017,776 B2
(45) Date of Patent: Jul. 10, 2018

(54) TRANSGENIC PLANTS WITH ALTERED NITRATE LEVELS IN LEAVES

(71) Applicant: BRITISH AMERICAN TOBACCO (INVESTMENTS) LIMITED, London (GB)

(72) Inventors: Susan Davenport, London (GB); Pascaline Le Lay, London (GB); Juan Pablo Sanchez Tamburrino, London (GB)

(73) Assignee: British American Tobacco (Investments) Limited, London (GB)

( * ) Notice: Subject to any disclaimer, the term of this patent is extended or adjusted under 35 U.S.C. 154(b) by 74 days.

(21) Appl. No.: 14/386,732

(22) PCT Filed: Mar. 19, 2013

(86) PCT No.: PCT/GB2013/050710
§ 371 (c)(1),
(2) Date: Sep. 19, 2014

(87) PCT Pub. No.: WO2013/140157
PCT Pub. Date: Sep. 26, 2013

(65) Prior Publication Data
US 2015/0034110 A1   Feb. 5, 2015

(30) Foreign Application Priority Data

Mar. 20, 2012 (GB) ................................. 1204871.6

(51) Int. Cl.
| | |
|---|---|
| *A01H 1/00* | (2006.01) |
| *C12N 15/82* | (2006.01) |
| *A24B 13/00* | (2006.01) |
| *A01H 15/00* | (2006.01) |
| *C12N 15/00* | (2006.01) |

(52) U.S. Cl.
CPC .......... *C12N 15/8225* (2013.01); *A24B 13/00* (2013.01); *C12N 15/8201* (2013.01); *C12N 15/8216* (2013.01); *C12N 15/8243* (2013.01); *C12N 15/8251* (2013.01)

(58) Field of Classification Search
None
See application file for complete search history.

(56) References Cited

U.S. PATENT DOCUMENTS

| 7,329,797 | B2 | 2/2008 | Schneeberger et al. |
| 2006/0143736 | A1 | 6/2006 | Schneeberger et al. |
| 2007/0044172 | A1 | 2/2007 | Schneeberger et al. |
| 2010/0162432 | A1* | 6/2010 | Puzio ............... C12N 15/8271 800/276 |
| 2011/0010797 | A1 | 1/2011 | Tsay et al. |
| 2011/0239324 | A1* | 9/2011 | Davenport ........... C12N 9/0044 800/278 |

FOREIGN PATENT DOCUMENTS

| EP | 0116718 A1 | 8/1984 |
| EP | 0242246 A1 | 10/1987 |
| EP | 0249637 A1 | 12/1987 |
| EP | 0270822 A1 | 6/1988 |
| EP | 0369637 A2 | 5/1990 |
| GB | 2197653 A | 5/1988 |
| WO | 87/03659 A1 | 6/1987 |
| WO | 00/39300 A1 | 7/2000 |
| WO | 2004/007730 A1 | 1/2004 |
| WO | 2006062971 A2 | 6/2006 |
| WO | 2009/105492 A2 | 8/2009 |
| WO | 2012/038717 A1 | 3/2012 |

OTHER PUBLICATIONS

Bevan, M.: "Binary Agrobacterium vectors for plant transformation", Nucleic Acids Research, vol. 12, No. 22, 1984, pp. 8711-8721.
Chiu C.-C.: "Mutation of a Nitrate Transporter, AtNRT1:4, Results in a Reduced Petiole Nitrate Content and Altered Leaf Development", Plant and Cell Physiology, 2004, vol. 45, No. 9, pp. 1139-1148.
Cornejo, M.-J. et al.: "Activity of a maize ubiquitin promoter in transgenic rice", Plant Molecular Biology, 1993, vol. 23, pp. 567-581.
Fan Shu-Chun et al.: "The Arabidopsis Nitrate Transporter NRT1.7, Expressed in Phloem, Is Responsible for Source-to-Sink Remobilization of Nitrate", The Plant Cell, Sep. 2009, vol. 21, No. 9, pp. 2750-2761.
Horsch, R. B. et al., "A Simple and General Method for Transferring Genes into Plants", Biological Sciences, 1985, vol. 227, pp. 1229-1231.
Hull R. et al., "The sequence of carnation etched ring virus DNA: comparison with cauliflower mosaic virus and retroviruses", The EMBO Journal, 1986, vol. 5, No. 12, pp. 3083-3090.
Kuluev B. R. et al.: "Activity of Promoters of Carnation Etched Ring Virus and Dahlia Mosaic Virus in Tobacco Protoplasts and Transgenic Plants", Russian Journal of Plant Physiology, 2008, vol. 55, No. 5, pp. 687-693.
Sharma A. et al.: "Determination of nitric oxide metabolites, nitrate and nitrite, in Anopheles culicifacies mosquito midgut and haemolymph by anion exchange high-performance liquid chromatography: plausible mechanism of refractoriness", Malaria Journal, 2008, 7:71.

(Continued)

*Primary Examiner* — Phoenix Bui
(74) *Attorney, Agent, or Firm* — McKee, Voorhees & Sease, PLC

(57) ABSTRACT

The present invention relates to genetic constructs, which can be used in the preparation of transgenic plants. The constructs can have the ability of reducing nitrate concentration in the plant, in particular the plant's leaves. The invention extends to plant cells transformed with such constructs, and to the transgenic plants themselves. The invention also relates to methods of producing transgenic plants, and to methods of reducing nitrate content in plants. The invention also relates to harvested plant leaves, for example tobacco leaves, that have been transformed with the genetic constructs, and to various tobacco articles, such as smoking articles, comprising such harvested plant leaves.

8 Claims, 8 Drawing Sheets

(56) References Cited

OTHER PUBLICATIONS

Figure 1:
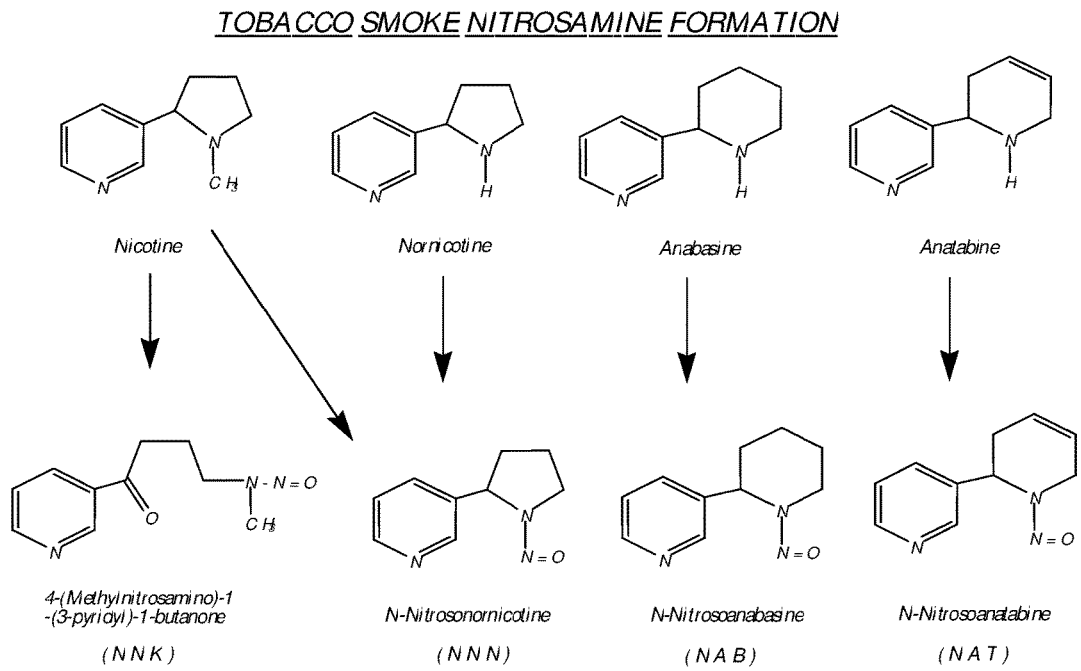

Thompson J. D. et al.: "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.
Thompson J. D. et al.: "The CLUSTAL_X windows interface: flexible strategies for multiple sequence alignment aided by quality analysis tools", Nucleic Acids Research, 1997, vol. 25, No. 24, pp. 4876-4882.
Van Engelen F. A. et al.: "pBINPLUS: an improved plant transformation vector based on pBIN19", Transgenic Research 1995, vol. 4, pp. 288-290.
Zhang W. et al., "Analysis of Rice Act1 5' Region Activity in Transgenic Rice Plants", The Plant Cell, Nov. 1991, vol. 3, pp. 1155-1165.
Database UniProt [Online] May 1, 2000, "RecName: Full=Nitrate transporter 1.4;", XP002699438.
Database UniProt [Online] Jun. 1, 2002, "RecName: Full=Nitrate transporter 1.7;", XP002699439.
International Search Report and Written Opinion, dated Jul. 10, 2013, for PCT/GB2013/050710.
Written Opinion of the International Preliminary Examining Authority, dated Mar. 10, 2014, for PCT/GB2013/050710.
International Preliminary Report on Patentability, dated Jun. 30, 2014, for PCT/GB2013/050710.

* cited by examiner pGNP024 0138 001 (T1283) map pGNP024 0139 001 (T1284) map

US 10,017,776 B2

TRANSGENIC PLANTS WITH ALTERED NITRATE LEVELS IN LEAVES

CROSS-REFERENCE TO RELATED APPLICATIONS

This application is the National Stage of International Patent Application Serial No. PCT/GB2013/050710, filed Mar. 19, 2013, which claims priority to and the benefits of Great British Patent Application Serial No. 1204871.6 filed Mar. 20, 2012, each of which is herein incorporated by reference in its entirety for all purposes.

TECHNICAL FIELD

The present invention relates to genetic constructs, which can be used in the preparation of transgenic plants. The constructs can have the ability of reducing nitrate concentration in the plant, in particular the plant's leaves. The invention extends to plant cells transformed with such constructs, and to the transgenic plants themselves.

The invention also relates to methods of producing transgenic plants, and to methods of reducing nitrate content in plants. The invention also provides methods for modifying plant amino acid profiles. The invention also relates to harvested plant leaves, for example tobacco leaves, that have been transformed with the genetic constructs, and to various tobacco articles, such as smoking articles, comprising such harvested plant leaves.

BACKGROUND

Nitrogen assimilation is of fundamental importance to the growth of plants. Of all the mineral nutrients required by plants, nitrogen is required in the greatest abundance.

The main forms of nitrogen taken up by plants in the field are nitrate and ammonia, the principle components of nitrogenous fertilizers. Plants take up either nitrate or ammonium ions from the soil, depending on availability. Nitrate will be more abundant in well-oxygenated, non-acidic soils, whilst ammonium will predominate in acidic or water-logged soils. Experiments on growth parameters of tobacco clearly demonstrated that relative growth rate, chlorophyll content, leaf area and root area increased dramatically in response to increasing nitrate supply.

Plants have developed an efficient nitrogen uptake system in order to cope with the large variation in nitrate content of cultivated soils. Plant roots take up nitrate and ammonia by the action of specific nitrate transporters (NTR), which are divided into two gene families, the NRT1 gene family and the NRT2 gene family. It is generally assumed that the NRT1 gene family mediates the low-affinity nitrate transport system (LATS, i.e. when the external nitrate concentration>1 mM), with the exception of the AtNRT1.1, which is both a dual affinity transporter and a nitrate sensor, while the NRT2 gene family mediates the high-affinity nitrate transport system (HATS, i.e. when the external nitrate concentration<1 mM). In *Arabidopsis*, 53 genes belong to the NRT1 family, however, only 51 of these genes are transcribed and each within various tissues.

This implies that the polypeptides that they encode possess specialized or unique functions. For example, Atnrt1.2 is constitutively expressed, but only within the root epidermis of *Arabidopsis*, where it participates in the constitutive low-affinity nitrate transport system.

Once within the roots of a plant, nitrate is then loaded into the xylem of the vascular stele where it is then distributed to other organs within the plant. It is known that the low affinity nitrate transporter, NRT1.5, plays a major role in loading nitrate, which is present within the roots, into xylem vessels. Once inside a cell, nitrate can be exported from vacuoles and transported towards growing organs, such as young leaves, when the availability of external supplies is limited or when mature leaves age and become a source leaves (i.e. leaves that pass on their nutrients to other tissues within a plant).

Nitrate remobilization is responsible for recycling nitrogen present within older leaves. It passes recycled nitrate onto younger leaves in order to sustain the growth of developing tissues. Nitrate remobilization also occurs between leaves and seeds, and is important for grain production and nitrogen recycling by senescent leaves. It is estimated that the contribution of leaf nitrogen remobilization to grain production is cultivar dependent, varying from 50 to 90%. Remobilized nitrogen may be in the form of amino acids released by proteolytic activity. However, inorganic nitrogen, in the form of nitrate, may also be remobilized. Thus, membrane proteins must transport nitrate through the plasma membrane towards the vascular tissues of source organs. Nitrate within source organs is then transported across the plasma membrane into the mesophyll cells. Here it is either stored in vacuoles, or reduced in the cytoplasm and enters the primary nitrogen assimilation pathway. When nitrate is present in excess, it is stored in the vacuole. This serves both as an osmoticum (i.e. supplements osmotic pressure), and as a source of mineral nitrogen to be used when nitrate uptake is minimal. The nitrate present in the cytoplasm is the starting point of primary nitrogen assimilation.

Nitrate is reduced in the cytosol by the cytoplasmic enzyme nitrate reductase to nitrite, which itself is rapidly reduced to ammonium by nitrite reductase (NiR) in the chloroplasts of leaves or in the plastids of non-photosynthetic organs. In the chloroplast, the ammonium then enters the glutamine synthetase/glutamate synthase cycle (GS/GOGAT), where it is incorporated into the amino acid pool.

The regulation of the activities of nitrate transporters, and nitrate and nitrite reductases is critical in controlling primary nitrogen assimilation throughout the plant, and has a significant impact on the growth and development of the plant. However, under certain conditions, nitrate may accumulate, mainly in green photosynthetically active tissues, where it is stored in the vacuoles of the mesophyll cells. High levels of nitrate accumulation can occur during periods of low temperature and/or solar irradiation (for example, in greenhouse crops during the winter), when there is less photosynthetic capacity to assimilate the stored nitrate, or as a result of high nitrate levels in the soil. An increase in nitrate levels can have a number of deleterious consequences, not only in terms of plant growth, but also in terms of human or animal health where the plant is consumed, as well as environmental consequences. Many of the adverse consequences of nitrate accumulation are mediated through the production of nitrite.

Therefore, to prevent nitrate accumulation, one strategy would be increasing nitrogen remobilisation in plants, for example when they become senescent, which could have important applications in crop production. Firstly, nitrogen remobilised from leaves can be transported to the younger leaves as well as the developing seed. Increasing the efficiency of nitrogen exit from senescent leaves could therefore potentially increase nitrogen supply to seeds and younger parts of the plant, and thereby increase crop yield and nitrogen use efficiency. This is clearly a valuable goal when the world population is increasing but crop yields are not increasing sufficiently to meet demand. One potential target crop is *Brassica napus* (oilseed rape), which has poor nitrogen efficiency due to poor nitrogen remobilisation from vegetative tissue. Another target crop is wheat, as the potential benefits of increasing grain protein content are great. Grain protein content not only affects nutritive value of wheat, but also determines grain usage and therefore market value. For example, increased grain protein content results in increased bread volume.

Also, an ability to increase nitrogen remobilisation could be very useful in the tobacco industry because it is known that residual nitrogen in tobacco leaves contributes to the formation of nitrosamines, as illustrated in FIG. 1. In particular, nitrate and nitrite act as precursors to tobacco-specific nitrosamine (TSNA) formation in cured leaf. The processing of the tobacco leaves by the tobacco industry involves the removal of petioles and mid-ribs of the cured leaves which are believed to act as nitrate storage organs, devoid of flavour and high in TSNAs. Also, the formation of nitrosamines in the stomach is a result of endogenous nitrosation. Oral bacteria chemically reduce nitrate consumed in food and drink to nitrite, which can form nitrosating agents in the acidic environment of the stomach. These react with amines to produce nitrosamines and cause DNA strand breaks or cross linking of DNA. Another problem associated with an excess of nitrate is the formation of methaemoglobin which gives rise to blue baby syndrome, where the oxygen carrying capacity of haemoglobin is blocked by nitrite, causing chemical asphyxiation in infants.

As a consequence of these health concerns, a number of regulatory authorities have set limits on the amount of nitrate allowed in leafy green vegetables such as spinach and lettuce (e.g. European Commission Regulation 653/2003), depending on the time of harvest. These limits have resulted in any produce with a high nitrate content being to unmarketable. Consequently, there have been efforts to reduce nitrate content of plants by managing the application of nitrogen-containing fertilisers or improved systems of crop husbandry. Some authorities have also set limits on the amounts of nitrate in drinking water.

There is therefore a need for means for alleviating the adverse effects associated with nitrate accumulation in plants. With this in mind, the inventors have developed a series of genetic constructs, which may be used in the preparation of transgenic plants, which exhibit surprisingly reduced nitrate concentrations.

SUMMARY OF THE INVENTION

Thus, according to a first aspect of the invention, there is provided a genetic construct comprising a promoter operably linked to a coding sequence encoding a polypeptide having low affinity nitrate transporter activity, with the proviso that the promoter is not a cauliflower mosaic virus 35S promoter.

As described in the Examples, the inventors have investigated the remobilisation of nitrogen in a plant, with a view to developing plants which exhibit decreased concentrations of nitrate, especially in the leaves. The inventors prepared a number of genetic constructs (see FIG. 2), in which a gene encoding a low nitrate transporter protein was placed under the control of a promoter, which was not the CAMV 35S promoter, such as a constitutive promoter or a tissue-specific promoter. Low affinity nitrate transporters mediate the low-affinity nitrate transport system (LATS), i.e. when the external nitrate concentration is greater than about 1 mM.

In one embodiment, the coding sequence in the construct may encode the *Arabidopsis* nitrate transporter, AtNRT1.4, which is a low affinity nitrate transporter. The cDNA sequence (exons only) encoding the *Arabidopsis* Nrt1.4 nitrate transporter is provided herein as SEQ ID No.1, as follows:

[SEQ ID No. 1]
ATGGAGAGCAAAGGGAGTTGGACAGTGGCTGATGCCGTAGACTACAAAG

GACGACCTGCCGACAAATCCAAAACCGGTGGTTGGATCACTGCCGCTCT

CATTCTTGGGATAGAAGTTGTGGAGAGGCTATCAACAATGGGAATAGCA

GTGAATTTGGTAACATATTTGATGGAGACAATGCATCTCCCAAGTTCAA

CCTCTGCCAACATTGTCACTGATTTCATGGGCACTTCCTTCCTCCTATG

CTTGCTCGGTGGTTTTCTCGCTGACTCCTTCCTCGGCCGTTTCAAAACC

ATCGGCATTTTCTCAACCATTCAAGCTCTGGGAACTGGTGCTCTAGCGG

TAGCAACTAAGCTGCCAGAGCTACGTCCACCAACATGCCATCATGGAGA

AGCTTGCATACCCGCGACCGCCTTCCAAATGACAATTCTTTATGTTTCG

CTTTACCTTATAGCCCTTGGAACTGGTGGTCTTAAATCTAGTATCTCTG

GATTTGGGTCTGACCAGTTTGATGACAAAGATCCTAAAGAGAAAGCTCAC

ATGGCTTTCTTCTTCAACAGGTTCTTCTTCTTTATTAGTATGGGGACAT

TATTGGCTGTGACTGTTTTAGTTTACATGCAAGATGAAGTGGGAAGATC

TTGGGCTTATGGAATCTGCACTGTCTCTATGGCTATAGCTATTGTAATA

TTCTTGTGTGGGACTAAGAGATACCGTTATAAGAAGAGCCAAGGAAGTC

CCGTTGTGCAAATATTTCAGGTCATAGCAGCTGCGTTCCGAAAGAGGAA

AATGGAACTACCTCAAAGCATTGTTTATCTTTATGAAGATAACCCTGAA

GGCATTAGAATTGAACATACTGATCAGTTTCACTTGTTGGACAAGGCGG

CCATAGTTGCAGAAGGAGATTTTGAACAAACCCTTGATGGAGTTGCAAT

CCCAAACCCTTGGAAGCTAAGCTCAGTGACCAAAGTTGAGGAAGTAAAA

ATGATGGTTAGGCTTTTGCCTATTTGGGCAACAACTATAATTTTTTGGA

CAACATATGCCCAAATGATTACATTCTCTGTTGAGCAAGCTTCAACTATG

AGACGTAACATTGGAAGCTTTAAGATCCCAGCTGGTTCCCTCACCGTGT

TTTTCGTTGCGGCTATTCTCATAACTCTAGCTGTCTACGACCGTGCCAT

AATGCCTTTTTGGAAGAAATGGAAAGGAAAACCAGGTTTCTCTAGCCTA

CAAAGAATAGCTATTGGATTGGTCTTATCAACCGCTGGAATGGCAGCTG

CAGCTCTAGTAGAGCAAAAGCGTTTATCCGTTGCGAAATCTAGTTCACA

AAAAACATTGCCTATAAGTGTGTTTTTACTTGTTCCACAATTCTTCTTA

GTAGGAGCTGGGGAAGCCTTTATCTACACTGGCCAACTTGATTTCTTCA

TAACACAATCGCCTAAGGGAATGAAAACTATGAGCACTGGACTCTTCTT

GACCACTTTATCACTAGGTTTCTTTGTCAGCAGTTTCTTGGTCTCAATC

GTCAAGAGGGTCACTTCAACTTCTACTGATGTAGGATGGCTGGCTGATA

ACATTAACCACGGCCGACTCGATTACTTTTATTGGCTTTTAGTCATTCTC

AGTGGAATTAACTTCGTTGTCTATATCATATGTGCCTTGTGGTTTAAGC

CAACGAAGGGTAAAGACTCAGTAGAGAAGGAAAATGGCAAGGGATTTTC

AGTTGAAGACTGCTGA

The polypeptide sequence of the *Arabidopsis* Nrt1.4 nitrate transporter is provided herein as SEQ ID No.2, as follows:

[SEQ ID No. 2]
MESKGSWTVADAVDYKGRPADKSKTGGWITAALILGIEVVERLSTMGIA

VNLVTYLMETMHLPSSTSANIVTDFMGTSFLLCLLGGFLADSFLGRFKT

IGIFSTIQALGTGALAVATKLPELRPPTCHHGEACIPATAFQMTILYVS

LYLIALGTGGLKSSISGFGSDQFDDKDPKEKAHMAFFFNRFFFFISMGT

LLAVTVLVYMQDEVGRSWAYGICTVSMAIAIVIFLCGTKRYRYKKSQGS

PVVQIFQVIAAAFRKRKMELPQSIVYLYEDNPEGIRIEHTDQFHLLDKAA

IVAEGDFEQTLDGVAIPNPWKLSSVTKVEEVKMMVRLLPIWATTIIFWT

TYAQMITFSVEQASTMRRNIGSFKIPAGSLTVFFVAAILITLAVYDRAI

MPFWKKWKGKPGFSSLQRIAIGLVLSTAGMAAAALVEQKRLSVAKSSSQ

KTLPISVFLLVPQFFLVGAGEAFIYTGQLDFFITQSPKGMKTMSTGLFL

TTLSLGFFVSSFLVSIVKRVTSTSTDVGWLADNINHGRLDYFYWLLVIL

SGINFVVYIICALWFKPTKGKDSVEKENGKGFSVEDC*

The * in the above sequence refers to the stop codon at the 3' end of the sequence, and is required for termination of expression. In another embodiment, the coding sequence in the construct may encode the *Arabidopsis* nitrate transporter, AtNRT1.7, which is also a low affinity nitrate transporter.

The cDNA sequence (exons only) encoding the *Arabidopsis* Nrt1.7 nitrate transporter is provided herein as SEQ ID No.3, as follows:

[SEQ ID No. 3]
ATGGTTTTGGAGGATAGAAAGGACGGTTCTTCTTTGCCGGGACGATCCG

GTAGTTTCTCTAAATCGTCACCGTCGGAGTTGGATGTTGTTGATCCCTA

CAAGCGGATAAGTTCGCCGGGATCTATATTGGATGCTGAGAAGGTAGAG

AAAAAGCCTGGAGGATGGAGAGCCGTCTCGTTCATTTTAGGAAATGAGA

CGCTGGAGAGACTGGGATCGATAGGATTGTTGGCAAACTTCATGGTTTA

TCTAACCAAAGTGTTTCACTTAGAACAAGTCGACGCTGCAAATGTCATC

AACATTTGGTCAGGTTTCACCAATCTCACTCCTCTCGTCGGAGCGTATA

TCTCAGACACTTATGTTGGCCGCTTCAAGACCATCGCTTTCGCCTCATT

CGCCACTCTCCTCGGACTAATAACAATTACACTCACAGCATCGTTTCCT

CAACTCCACCCAGCATCATGCAACAGCCAGGACCCACTCAGTTGCGGCG

GTCCGAATAAGCTCCAGATCGGAGTTTTGCTATTGGGACTCTGTTTCCTC

TCCGTAGGGAGTGGAGGAATACGACCTTGTAGCATCCCTTTTGGGGTTG

ATCAGTTTGACCAACGAACTGAGGAAGGGGTTAAAGGAGTGGCCAGTTT

CTTCAACTGGTATTACATGACTTTCACTGTGGTTCTGATCATTACACAG

ACCGTAGTTGTGTATATCCAGGATCAAGTCAGTTGGATTATCGGTTTTA

GTATCCCTACCGGACTCATGGCTCTTGCCGTTGTTATGTTTTTTGCCGG

AATGAAGCGTTATGTCTACGTTAAACCAGAAGGAAGTATATTCTCTGGG

ATCGCTCAAGTTATCGTGGCAGCTCGTAAGAAGCGAAAGCTGAAACTTC

CGGCGGAAGATGACGGCACTGTCACCTATTACGACCCAGCCATCAAGTC

-continued
TAGCGTGTTATCCAAGTTACACCGCAGTAACCAATTCAGGTGTCTTGAC

AAAGCCGCGGTGGTTATAGAAGGTGACCTAACACCCGAGGGACCTCCCG

CAGACAAGTGGCGGTTATGCAGCGTCCAAGAAGTGGAAGAAGTGAAGTG

TTTGATCCGAATTGTTCCTATCTGGTCGGCCGGAATAATCTCACTCGCG

GCCATGACAACACAAGGCACTTTCACGGTCTCTCAAGCTTTGAAAATGG

ATCGAAACTTAGGTCCTAAATTCGAGATTCCGGCTGGTTCACTCTCCGT

CATCTCTCTCCTCACAATCGGCATCTTTCTTCCCTTCTACGACCGCGTT

TTTGTACCATTCATGCGGCGAATCACCGGCCATAAATCCGGAATCACAC

TCCTCCAAAGGATAGGAACAGGGATCGTTTTCGCGATCTTTTCTATGAT

CGTTGCGGGCATTGTGGAGCGTATGAGACGCATACGCTCCATCAATGCC

GGAGATCCAACGGGAATGACTCCAATGTCGGTGTTTTGGCTTTCGCCGC

AGCTAATTCTCATGGGACTATGTGAAGCATTCAATATCATCGGACAAAT

TGAGTTCTTCAACAGTCAGTTTCCAGAGCACATGAGAAGTATCGCTAAC

TCTCTCTTCTCTTTATCGTTCGCCGGTTCGAGCTACCTTAGTAGTTTCC

TTGTGACTGTCGTTCATAAATTCTCCGGTGGGCATGATCGTCCGGATTG

GCTAAACAAGAATCTCAACGCGGGAAAATTGGATTACTTCTATTATCTG

ATTGCGGTTTTGGGTGTGGTTAATCTGGTTTACTTTTGGTATTGTGCTC

GGGGATACCGGTACAAGGTCGGTTTACCGATTGAAGACTTTGAGGAGGA

CAAGTCCTCCGATGATGTTGAGATGACTTCGAAGAAATCGATGAAATGA

The polypeptide sequence of the *Arabidopsis* Nrt1.7 nitrate transporter is provided herein as SEQ ID No.4, as follows:

[SEQ ID No. 4]
MVLEDRKDGSSLPGRSGSFSKSSPSELDVVDPYKRISSPGSILDAEKVE

KKPGGWRAVSFILGNETLERLGSIGLLANFMVYLTKVFHLEQVDAANVI

NIWSGFTNLTPLVGAYISDTYVGRFKTIAFASFATLLGLITITLTASFP

QLHPASCNSQDPLSCGGPNKLQIGVLLLGLCFLSVGSGGIRPCSIPFGV

DQFDQRTEEGVKGVASFFNWYYMTFTVVLIITQTVVVYIQDQVSWIIGF

SIPTGLMALAVVMFFAGMKRYVYVKPEGSIFSGIAQVIVAARKKRKLKLP

AEDDGTVTYYDPAIKSSVLSKLHRSNQFRCLDKAAVVIEGDLTPEGPPA

DKWRLCSVQEVEEVKCLIRIVPIWSAGIISLAAMTTQGTFTVSQALKMD

RNLGPKFEIPAGSLSVISLLTIGIFLPFYDRVFVPFMRRITGHKSGITL

LQRIGTGIVFAIFSMIVAGIVERMRRIRSINAGDPTGMTPMSVFWLSPQ

LILMGLCEAFNIIGQIEFFNSQFPEHMRSIANSLFSLSFAGSSYLSSFL

VTVVHKFSGGHDRPDWLNKNLNAGKLDYFYYLIAVLGVVNLVYFWYCARG

YRYKVGLPIEDFEEDKSSDDVEMTSKKSMK*

The * in the above sequence refers to the stop codon at the 3' end of the sequence, and is required for termination of expression. Accordingly, the polypeptide having low affinity nitrate transporter activity may comprise an amino acid sequence substantially as set out in either SEQ ID No.2 or SEQ ID No.4, or a functional variant or fragment or orthologue thereof. Furthermore, the coding sequence, which encodes the polypeptide having low affinity nitrate transporter activity, may comprise a nucleic acid sequence substantially as set out in either SEQ ID No.1 or SEQ ID No.3, or a functional variant or fragment or orthologue thereof.

The promoter may be capable of inducing RNA polymerase to bind to, and start transcribing, the coding sequence encoding the polypeptide having nitrate transporter activity. The promoter in constructs of the invention may be a constitutive, non-constitutive, tissue-specific, developmentally-regulated or inducible/repressible promoter.

A constitutive promoter directs the expression of a gene throughout the various parts of the plant continuously during plant development, although the gene may not be expressed at the same level in all cell types. Examples of known constitutive promoters include those associated with the rice actin 1 gene (Zhang et al., 1991, Plant Cell, 3, 1155-65) and the maize ubiquitin 1 gene (Cornejo et al., 1993, Plant Molec. Biol., 23, 567-581). Constitutive promoters such as the Carnation Etched Ring Virus (CERV) promoter (Hull et al., 1986, EMBO J., 5, 3083-3090) are particularly preferred in the present invention.

A tissue-specific promoter is one which directs the expression of a gene in one (or a few) parts of a plant, usually throughout the life-time of those plant parts. The category of tissue-specific promoter commonly also includes promoters whose specificity is not absolute, i.e. they may also direct expression at a lower level in tissues other than the preferred tissue. Examples of tissue-specific promoters known in the art include those associated with the patatin gene expressed in potato tuber, and the high molecular weight glutenin gene expressed in wheat, barley or maize endosperm.

A developmentally-regulated promoter directs a change in the expression of a gene in one or more parts of a plant at a specific time during plant development, e.g. during senescence. The gene may be expressed in that plant part at other times at a different (usually lower) level, and may also be expressed in other plant parts.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter can be described as a specific type of inducible promoter responding to an endogenous inducer produced by the plant or to an environmental stimulus at a particular point in the life cycle of the plant. Examples of known inducible promoters include those associated with wound response, temperature response, and chemically induced.

The promoter may be obtained from different sources including animals, plants, fungi, bacteria, and viruses, and different promoters may work with different efficiencies in different tissues. Promoters may also be constructed synthetically. Therefore, examples of suitable promoters include the Carnation Etched Ring Virus (CERV) promoter, the pea plastocyanin promoter, the rubisco promoter, the nopaline synthase promoter, the chlorophyll a/b binding promoter, the high molecular weight glutenin promoter, the a,J3-gliadin promoter, the hordein promoteror the patatin promoter.

Preferably, the promoter is the CERV promoter, as shown in the constructs illustrated in FIG. 2.

Thus, according to a second aspect of the invention, there is provided a genetic construct comprising a Carnation Etched Ring Virus (CERV:) promoter operably linked to a coding sequence encoding a polypeptide having low affinity nitrate transporter activity.

The polypeptide having low affinity nitrate transporter activity may comprise an amino acid sequence substantially as set out in either SEQ ID No.2 or SEQ ID No.4, or a functional variant or fragment or orthologue thereof.

The Carnation Etched Ring Virus (CERV) promoter will be known to the skilled technician (Hull et al., EMBO J., 5, 3083-3090). The DNA sequence encoding the CERV promoter is 232 bp long, and is referred to herein as SEQ ID No.5, as follows:

[SEQ ID No. 5]
AGCTTGCATGCCTGCAGGTCGAGCTTTTAGGATTCCATAGTGATAAGAT

ATGTTCTTATCTAAACAAAAAAGCAGCGTCGGCAAACCATACAGCTGTC

CACAAAAAGGAAAGGCTGTAATAACAAGCGGACCCAGCTTCTCAGTGGA

AGATACTTTATCAGACACTGAATAATGGATGGACCCTACCACGATTAAA

GAGGAGCGTCTGTCTAAAGTAAAGTAGAGCGTCTTT

Therefore, the promoter in the construct of the invention may comprise a nucleotide sequence substantially as set out in SEQ ID No.5, or a functional variant or functional fragment thereof. The CERV promoter may be obtained from Cauliovirus or a plant species such as *Dianthus caryophyllus* (i.e. carnation) showing signs of the cauliovirus. In embodiments where the promoter is the CERV promoter, it will be appreciated that the promoter may comprise each of the bases 1-232 of SEQ ID No.5. However, functional variants or functional fragments of the promoter may also be used in genetic constructs of the invention.

A "functional variant or functional fragment of a promoter" can be a derivative or a portion of the promoter that is functionally sufficient to initiate expression of any coding region that is operably linked thereto. For example, in embodiments where the promoter is based on the CERV promoter, the skilled technician will appreciate that SEQ ID No.5 may be modified, or that only portions of the CERV promoter may be required, such that it would still initiate gene expression in the construct.

Functional variants and functional fragments of the promoter may be readily identified by assessing whether or not transcriptase will bind to a putative promoter region, and then lead to the transcription of the coding region into the polypeptide having nitrate transporter activity. Alternatively, such functional variants and fragments may be examined by conducting mutagenesis on the promoter, when associated with a coding region, and assessing whether or not gene expression may occur.

The polypeptide having nitrate transporter activity in the construct of the first or second aspect may be derived from any suitable source, such as a plant. The coding sequence, which encodes the polypeptide having nitrate transporter activity, may be derived from a suitable plant source, for example from *Arabidopsis* spp., *Oryza* spp., *Populus* spp. or *Nicotiana* spp. The coding sequence may be derived from *Arabidopsis thaliana, Oryza sativa, Populus tremula* or *Nicotiana tabacum*. It will be appreciated that orthologues are genes or proteins in different species that evolved from a common ancestral gene by speciation, and which retain the same function.

The inventors have created two constructs in which the CERV promoter has been used to drive expression of the *Arabidopsis thaliana* nitrate transporter proteins, AtNRT1.4 and AtNrt1.7.

The construct may be capable of decreasing, in a plant transformed with a construct of the invention, the concentration of nitrate by at least 5%, 10%, 15%, 18%, 20%, 32%, 35%, 38%, 40%, 50%, 60% or 63%, compared to the concentration of nitrate in the wild-type plant (i.e. which has not been transformed with a construct of the invention), preferably grown under the same conditions.

The construct may be capable of decreasing, in a plant transformed with the construct, the concentration of 4-(Methylnitrosamino)-1-(3-pyridyl)-1-butanone (NNK) by at least 10%, 20%, 30%, 40%, 50%, 60%, 61%, 62%, 65%, 69%, 71% or 75% compared to the concentration of NNK in the wild-type plant, preferably grown under the same conditions.

The construct may be capable of decreasing, in a plant transformed with the construct, the concentration of N-Nitrosonornicotine (NNN) by at least 10%, 20%, 30%, 40%, 50%, 60%, 70%, 71%, 75%, 78%, 80%, 82%, 84%, 85%, 88%, 90% or 94% compared to the concentration of NNN in the wild-type plant, preferably grown under the same conditions.

The construct may be capable of decreasing, in a plant transformed with the construct, the concentration of N-Nitrosoanatabine (NAT) by at least 5%, 6%, 10%, 20%, 23%, 24%, 30%, 40%, 46%, 45%, 48%, 50%, 60%, 70%, 80% or 85% compared to the concentration of NAT in the wild-type plant, preferably grown under the same conditions.

The construct may be capable of decreasing, in a plant transformed with the construct, the concentration of total tobacco-specific nitrosamines (TSNA) by at least 10%, 20%, 30%, 40%, 50%, 56%, 60%, 64%, 65%, 70% or 75% compared to the concentration of total TSNA in the wild-type plant, preferably grown under the same conditions.

Preferably, the construct is capable of decreasing the concentration of any of the compounds selected a group of compounds including nitrate, NNK, NNN, NAT and total TSNA, in a leaf or stem from a plant of a T0, T1 and/or T2 plant population. The inventors have shown in the Examples that over-expression of AtNrt1.4 and AtNrt1.7 results in increased remobilisation of nitrate in the leaf in the test or transgenic plant compared to that of the wild-type. This nitrate remobilisation is believed to be mediated through remobilisation of amino acids either in or out of the leaf. This is demonstrated by lower levels of the amino acids, Glu, Asp, Pro, Gln and Asn, being present in the sink leaves (i.e. top leaves) of plants that over-express either the AtNrt1.4 construct or the AtNrt1.7 construct; lower levels of the amino acids, Glu, Asp, Pro, Gln and Asn, being present in the source tissues (i.e. lower leaves) of plants that over-express the AtNrt1.4 construct; higher levels of the amino acids, Glu, Asp and Pro, being present in the source tissues of plants that over-express the AtNrt1.7 construct; and lower levels of the amino acids, Gln and Asn, being present in the source tissues of plants that over-express the AtNrt1.7 construct (see the Figures). The construct may therefore be capable of either decreasing or increasing the concentration of various amino acids in the lower, middle or upper leaves of a plant.

The construct may be capable of decreasing the concentrations of any of these compounds (i.e. nitrate, amino acids involved in nitrogen assimilation, total TSNA, NNN, NAT or NNK) in a leaf located at a lower, middle or upper position on the plant. "Lower position" can mean in the lower third of the plant (for example leaf number 4 or 5 from the base of the plant), "upper position" can mean in the upper third of the plant (for example leaf number 14 or 15 from the base of the plant), and "middle position" can mean the central third of the plant between the lower and upper positions (for example leaf number 10 or 11 from the base of the plant). At the time of sampling, the total number of leaves is approximately 20.

Genetic constructs of the invention may be in the form of an expression cassette, which may be suitable for expression of the coding sequence encoding a nitrate transporter in a host cell. The genetic construct of the invention may be introduced into a host cell without it being incorporated in a vector. For instance, the genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly into cells of a host subject (e.g. a plant) by transfection, infection, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Hence, in a third aspect, there is provided a recombinant vector comprising the genetic construct according to the first or second aspect.

The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both $E.$ $coli$ and $Agrobacterium$ $tumefaciens$. For example, a suitable vector may be a pBIN plasmid, such as pBIN19 (Bevan M., 1984, Nucleic Acids Research 12:8711-21).

Recombinant vectors may include a variety of other functional elements in addition to the promoter (e.g. a CERV), and the coding sequence encoding a nitrate transporter. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector of the third aspect may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sul respectively; EP-A-242246, EP0369637A2); and screenable markers such as beta-glucuronidase (GB2197653), luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

The various embodiments of genetic constructs of the invention may be prepared using the cloning procedure described in the Examples, which may be summarised as follows. The genomic or cDNA versions of the genes encoding the nitrate transporter may be amplified from the genomic or cDNA templates by PCR using suitable primers, for example SEQ ID No's 6 and 7, or SEQ ID No's 8 and 9. PCR products may then be examined using agarose gel electrophoresis. The PCR products may then be introduced into a suitable vector for cloning purposes, for example pDONR™ zeo (Invitrogen), which is suitable for both Nrt1.4 and Nrt1.7. Vectors harbouring the PCR products may be grown up in a suitable host, such as *E. coli*. *E. coli* colonies may then be screened using a restriction digest, with HindIII, to determine if either Atnrt1.4 or Atnrt1.5 have been incorporated into the pDONR™ zeo vector. Inserts in plasmids showing the correct restriction enzyme digest pattern may be sequenced using suitable primers.

*E. coli* colonies carrying the pDONR™ zeo entry vector and cDNA or genomic DNA for either Atnrt1.4 or Atnrt1.7 may be cultured to produce a suitable amount of each plasmid, which may then be purified. The plasmids may then be digested to release a DNA fragment encoding the Atnrt1.4 or the Atnrt1.7 gene, which may then be cloned into a vector, such as a pBNP plasmid (van Engelen et al., 1995, Transgenic Research, 4:288-290), harbouring a suitable promoter, for example the CERV promoter.

The resultant Atnrt1.4 and Atnrt1.7 constructs, contained the CERV promoter and were named CRVAtNRT1.4 and CRVAtNRT1.7 respectively. Embodiments of the vector according to the third aspect may be substantially as set out in FIG. 2.

The inventors believe that they are the first to have developed a method for decreasing to nitrate concentrations in plant leaves using the expression of the exogenous nitrate transporter genes Atnrt1.4 and Atnrt1.7 in a transgenic plant.

Hence, in a fourth aspect, there is provided a method of decreasing the nitrate concentration in the leaves of a test plant to below that of the corresponding nitrate concentration in leaves of a wild-type plant cultured under the same conditions, the method comprising:—
(i) transforming a plant cell with the genetic construct according to the first or second aspect, or the vector according to the third aspect; and
(ii) regenerating a plant from the transformed cell.

In a fifth aspect of the invention, there is provided a method of producing a transgenic plant which transports nitrate out of a leaf at a higher rate than a corresponding wild-type plant cultured under the same conditions, the method comprising:—
(i) transforming a plant cell with the genetic construct according to the first or second aspect, or the vector according to the third aspect; and
(ii) regenerating a plant from the transformed cell.

In a sixth aspect, there is provided a method for producing a transgenic plant, the method comprising introducing, into an unmodified plant, an exogenous gene encoding a low affinity nitrate transporter polypeptide, wherein expression of the nitrate transporter encoded by the exogenous gene reduces the nitrate concentration in the leaves of the transgenic plant relative to the concentration of nitrate in the leaves of the unmodified plant.

The position of a leaf in relation to the rest of the plant (i.e. whether it is regarded as being within the "lower" position, the "top" position or the "middle" position) is important for tobacco growers. The physiology, and therefore, the quality and the flavour of a leaf are strongly related to its position within a plant. As a plant approaches flowering, a process called remobilization occurs, and it involves the transport of nutrients, such as amino acids and nitrogenous compounds, from the base of the plant towards the top of the plant. Remobilized nutrients will be used as an energy source for seed production. Consequently, the lower leaves will have a different nitrogen content compared to the upper leaves of the plant, which is illustrated by a different amino acid profile. Lower leaves are called "source leaves" and the top leaves are called "sink leaves". The middle leaves are fully expanded mature green leaves.

With respect to some plants, such as tobacco, by removing the flower head of the plant, changes in leaf nutrient metabolism can be generated. These changes allow the remobilized nutrients to be used in the leaves, and result in thickened leaves, general growth of the leaves and the production of nitrogen-rich secondary metabolites, many of which are the precursors of the flavours that are later found in cured leaves. Therefore, constructs of the invention may be used to modify the flavour of a transgenic plant.

As shown in FIGS. 3 to 8, the inventors were surprised to observe that the genetic constructs according to the invention may also be capable of modulating (i.e. increasing and/or decreasing) the concentration of certain amino acids that are known to involved in nitrate metabolism (e.g. Gln, Asn, Asp, Glu and/or Pro), in the leaves of a transgenic plant, which are found in the upper, middle or lower position, compared to corresponding leaves that are found in a wild-type plant grown under the same conditions.

Accordingly, in a seventh aspect, there is provided a method of modulating the profile of amino acids involved in the nitrogen assimilation of leaves of a test plant compared to the amino acid profile of corresponding leaves of a wild-type plant cultured under the same conditions, the method comprising:—
(i) transforming a plant cell with the genetic construct according to the first or second aspect, or the vector according to the third aspect; and
(ii) regenerating a plant from the transformed cell.

In an eighth aspect, there is provided a method of modulating the profile of amino acids involved in the nitrogen assimilation pathway of a harvested leaf taken from a transgenic plant, compared to the amino acid profile of a corresponding harvested leaf taken from a wild-type plant cultured under the same conditions, wherein the leaf is harvested from a transgenic plant produced by the method according to either the fifth or sixth aspect.

According to the invention, amino acids involved in the nitrogen assimilation pathway of plants and their leaves may comprise glutamine (Gln), asparagine (Asn), aspartic acid (Asp), glutamic acid (Glu) or proline (Pro), and so any of the profile or any or all of these amino acids may be modulated.

The construct may be capable of either decreasing or increasing, in a plant transformed with the construct, the concentration of at least one amino acid involved in the nitrogen assimilation pathway by at least 10%, 20%, 30%, 40%, 50%, 56%, 60%, 64%, 65%, 70% or 75% compared to the concentration of the at least one amino acid in a wild-type plant grown under the same conditions.

Preferably, the construct results in the decrease in concentration of the amino acid. Preferably, the construct encoding a nitrate transporter with Nrt1.4 activity may be capable of decreasing the concentration of the amino acids, Glu, Asp, Pro, Gln and/or Asn, in the leaves (preferably the lower and upper leaves) of a transgenic plant compared to corresponding leaves that are found in a wild-type plant grown under the same conditions.

Preferably, the construct encoding a nitrate transporter with Nrt1.7 activity may be capable of decreasing the concentration of the amino acids, Glu, Asp, Pro, Gln and/or Asn, in the leaves (preferably the upper leaves) of a transgenic plant compared to corresponding leaves that are found in a wild-type plant grown under the same conditions. Preferably, the construct encoding a nitrate transporter with Nrt1.7 activity may be capable of decreasing the concentration of the amino acids, Gln and/or Asn, in the leaves (preferably the lower leaves) of a transgenic plant compared to corresponding leaves that are found in a wild-type plant grown under the same conditions.

Surprisingly, and preferably, the construct encoding a nitrate transporter with Nrt1.7 activity may also be capable of increasing the concentration of the amino acids, Glu, Asp and/or Pro, in the leaves (preferably the lower leaves) of a transgenic plant compared to corresponding leaves that are found in a wild-type plant grown under the same conditions.

In a ninth aspect, there is provided a transgenic plant comprising the genetic construct according to the first or second aspect, or the vector according to the third aspect.

In an tenth aspect, there is provided a transgenic plant comprising an exogenous gene encoding a low affinity nitrate transporter polypeptide, wherein the nitrate concentration in the leaves of the transgenic plant is reduced compared to the nitrate concentration in the leaves of an unmodified plant.

In a eleventh aspect, there is provided use of an exogenous nucleic acid sequence encoding a low affinity nitrate transporter polypeptide for reducing the nitrate concentration in plant leaves by transformation of the plant with the exogenous nucleic acid sequence.

The term "unmodified plant" can mean a plant before transformation with an exogenous gene or a construct of the invention. The unmodified plant may therefore be a wild-type plant.

The term "exogenous gene" can mean the gene that is transformed into the unmodified plant is from an external source, i.e. from a different species to the one being transformed. The exogenous gene may have a nucleic acid sequence substantially the same or different to an endogenous gene encoding a nitrate transporter in the unmodified plant. The exogenous gene may be derived from a genomic or cDNA sequence encoding either the *Arabidopsis thaliana* nrt1.4 gene or the *Arabidopsis thaliana* nrt1.7 gene or an orthologue thereof. The exogenous gene may form a chimeric gene, which may itself constitute a genetic construct according to the first or second aspect. The exogenous gene may encode a low affinity nitrate transporter having the amino acid sequence substantially as set out in either SEQ ID No.2 or SEQ ID No.4, or a functional variant or fragment or orthologue thereof. The exogenous gene may comprise the nucleotide sequence substantially as set out in either SEQ ID No.1 or SEQ ID No.3, or a functional variant or fragment or orthologue thereof.

The methods and uses of the invention may comprise transforming a test plant cell or unmodified plant cell with a genetic construct according to the first or second aspect, a vector according to the third aspect, or the exogenous gene described herein.

Thus, in a twelfth aspect, there is provided a host cell comprising the genetic construct according to the first or second aspect, or the recombinant vector according to the third aspect.

The cell may be a plant cell. The cell may be transformed with a genetic construct, vector or exogenous gene according to the invention, using known techniques. Suitable means for introducing the genetic construct into the host cell may include use of a disarmed Ti-plasmid vector carried byAgrobacterium by procedures known in the art, for example as described in EP-A-0116718 and EP-A-0270822. A further method may be to transform a plant protoplast, which involves first removing the cell wall and introducing the nucleic acid, and then reforming the cell wall. The transformed cell may then be grown into a plant.

Preferably, and advantageously, the methods and uses according to the invention do not compromise the health or fitness of the test or transgenic plant that is generated. The transgenic or test plants according to invention may include the Brassicaceae family, such as *Brassica* spp. The plant may be *Brassica napus* (oilseed rape). Further examples of transgenic or test plants include the family Poales, such as *Triticeae* spp. The plant may be *Triticum* spp. (wheat). Increasing the grain protein content in wheat may result in increased volume of food products comprising wheat, such as bread.

Further examples of suitable transgenic or test plants according to the invention may include the Solanaceae family of plants which include, for example jimson weed, eggplant, mandrake, deadly nightshade (belladonna), *capsicum* (paprika, chilli pepper), potato and tobacco. One example of a suitable genus of Solanaceae is *Nicotiana*. A suitable species of *Nicotiana* may be referred to as tobacco plant, or simply tobacco.

Further examples of suitable transgenic or test plants according to the invention may include leafy crops such as the Asteraceae family of plants which, for example, include lettuce (*Lactuca sativa*). Another example may include the Chenopodiaceae family of plants, which includes *Spinacia oleracea* and *Beta vulgaris*, i.e. spinach and chards, respectively.

Tobacco may be transformed with constructs, vectors and exogenous genes of the invention as follows.

*Nicotiana tabacum* is transformed using the method of leaf disk co-cultivation essentially as described by Horsch et al. (Science 227: 1229-1231, 1985). The youngest two expanded leaves may be taken from 7-week old tobacco plants and may be surface-sterilised in 8% Domestos™ for 10 minutes and washed (3 rinses) times with sterile distilled water. Leaf disks may then be cut using a number 6 cork borer and placed in the *Agrobacterium* suspension, containing the appropriate binary vectors (according to the invention), for approximately two minutes. The discs may then be gently blotted between two sheets of sterile filter paper. Ten disks may be placed on MS 3% sucrose+2.2 µM BAP+0.271M NAA plates, which may then be incubated for 2 days in the growth room. Discs may then be transferred to plates of MS+3% sucrose+2.2 µM BAP+0.27 µM NAA supplemented with 500 g/l Cefotaxime and 100 g/l kanamycin. After 2 weeks, the discs may be transferred onto fresh plates of above medium. After a further two weeks, the leaf disks may be transferred onto plates containing LS+3% sucrose+0.5 μM BAP supplemented with 500 mg/l Cefotaxime and 100 mg/l kanamycin. The leaf disks may be transferred onto fresh medium every two weeks. Shoots may then be excised as they appear, and transferred to jars of LS media+3% sucrose+0.5M BAP supplemented with 500 mg/l claforan. The shoots may then be transferred, in jars, to LS media+3% sucrose+250 mg/l Cefotaxime after approximately 3 weeks. After a further 3-4 weeks the plants may be transferred to LS+3% sucrose (no antibiotics) and rooted. Once the plants are rooted they may be transferred to soil in the greenhouse.

In a thirteenth aspect, there is provided a plant propagation product obtainable from the transgenic plant according to either the ninth or tenth aspect.

A "plant propagation product" may be any plant matter taken from a plant from which further plants may be produced. Suitably, the plant propagation product may be a seed. The plant propagation product may preferably comprise a construct or vector according to the invention or an exogenous gene.

In a fourteenth aspect of the invention, there is provided a harvested leaf containing a lower level of nitrate than the corresponding level of nitrate in a harvested leaf taken from a wild-type plant cultured under the same conditions, wherein the leaf is harvested from the transgenic plant according to either the ninth or tenth aspect, or produced by the method according to either the fifth or sixth aspect.

In a fifteenth aspect of the invention, there is provided a tobacco product comprising nitrate-reduced tobacco obtained from a mutant tobacco plant comprising the construct of the first or second aspect or the vector of the third aspect, which mutant is capable of decreasing the concentration of nitrate in its leaves.

It is preferred that the mutant tobacco plant from which the tobacco in the tobacco product is derived comprises a construct, vector or exogenous gene according to the invention.

The tobacco product may be a smokeless tobacco product, such as snuff. The tobacco product may be an oral tobacco product deliverable by the mouth. The tobacco product may be moist, and may be snus. However, the tobacco product may also be a smoking article.

Thus, in a sixteenth aspect, there is provided a smoking article comprising nitrate-reduced tobacco obtained from a mutant tobacco plant comprising the construct of the first or second aspect or the vector of the third aspect, which mutant is capable of decreasing the concentration of nitrate in its leaves.

Nitrate-reduced tobacco can include tobacco in which the nitrate concentration is less than the corresponding concentration in a wild-type plant cultured under the same conditions. Such a smoking article may comprise tobacco obtained from a mutant tobacco plant, which may have been transformed with a genetic construct according to the first or second aspect of the invention, or a vector according to the third aspect, or an exogenous gene. Preferably, the mutant tobacco plant comprises either the nitrate transporter AtNRT1.4 or AtNRT1.7.

The term "smoking article" can include smokeable products, such as rolling tobacco, cigarettes, cigars and cigarillos whether based on tobacco, tobacco derivatives, expanded tobacco, reconstituted tobacco or tobacco substitutes and also heat-not-burn products.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the gene identified as SEQ ID No.1 (which encodes one embodiment of a nitrate transporter), or 40% identity with the polypeptide identified as SEQ ID No.2 (i.e. one embodiment of a nitrate transporter).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—
Sequence Identity=(N/T)*100.

Alternative methods for identifying similar sequences will be known to those skilled in the art. For example, a substantially similar nucleotide sequence will be encoded by a sequence which hybridizes to the sequences shown in either SEQ ID Nos. 1, 3, or 5, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in either SEQ ID No.2 or SEQ ID No.4.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

In order to address various issues and advance the art, the entirety of this disclosure shows by way of illustration various embodiments in which the claimed invention(s) may be practiced and provide for superior method for reducing the nitrate concentration in the leaves of transgenic plants. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 2A:
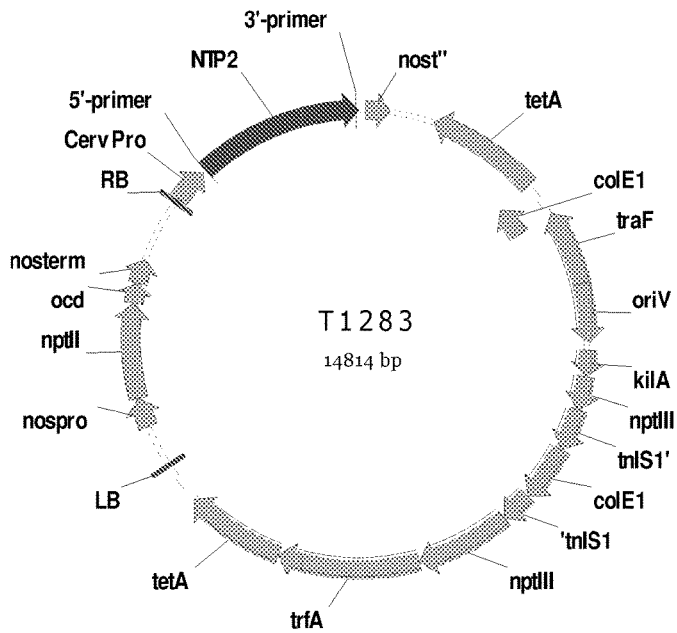
Figure 2B:
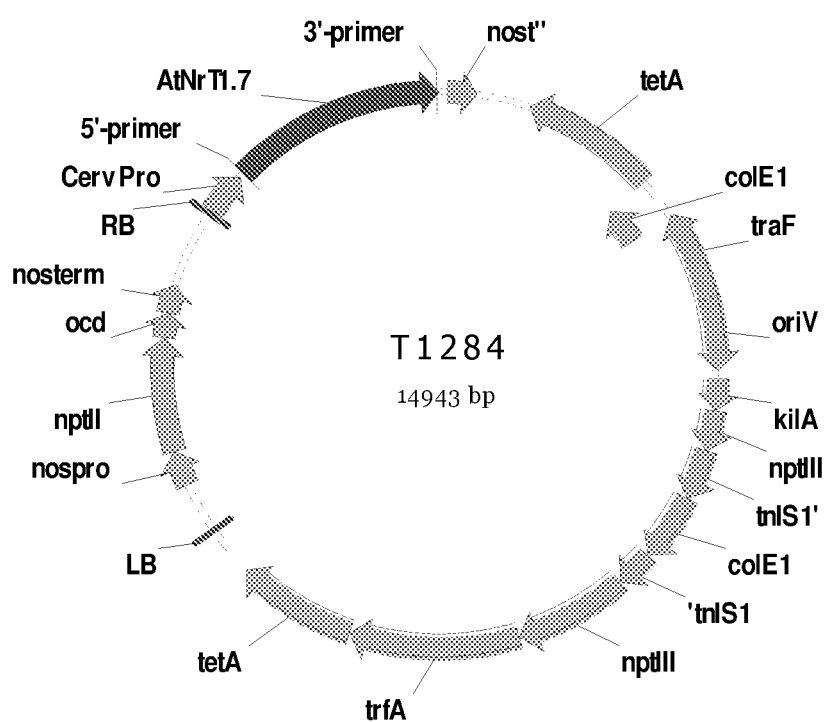
Figure 3A:
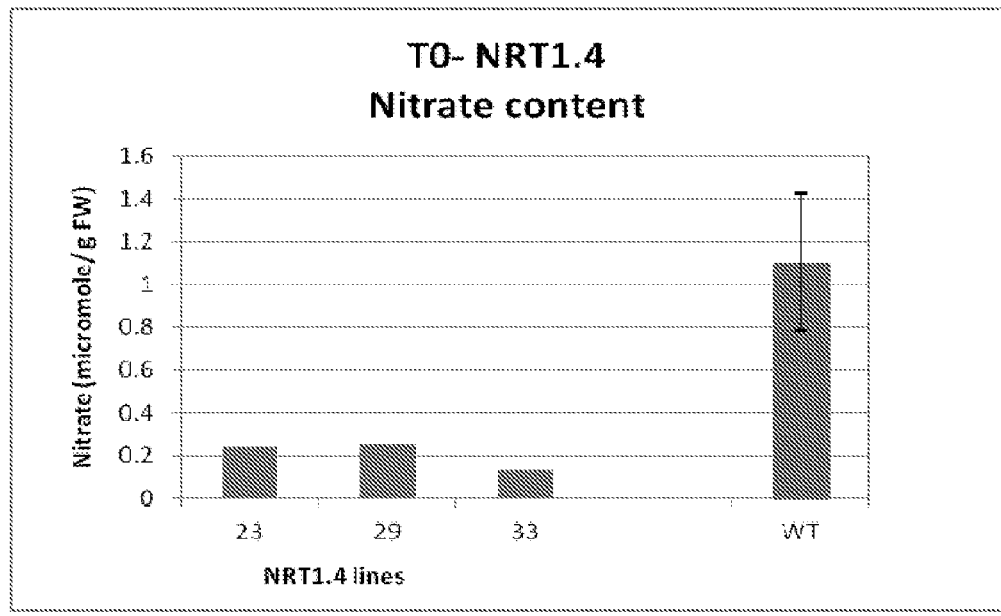
Figure 3B:
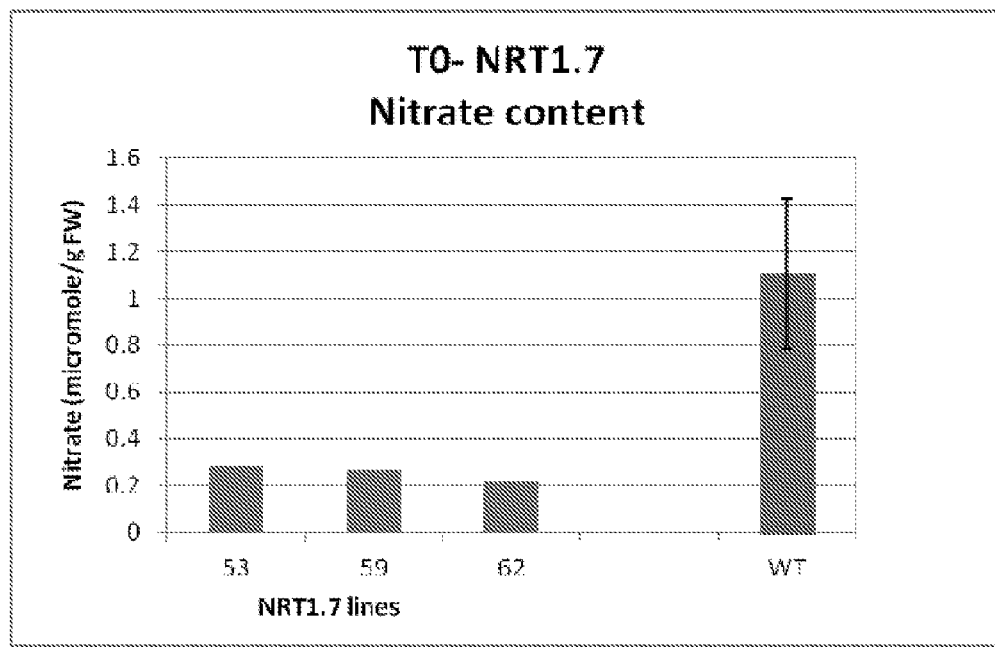
Figure 4A:
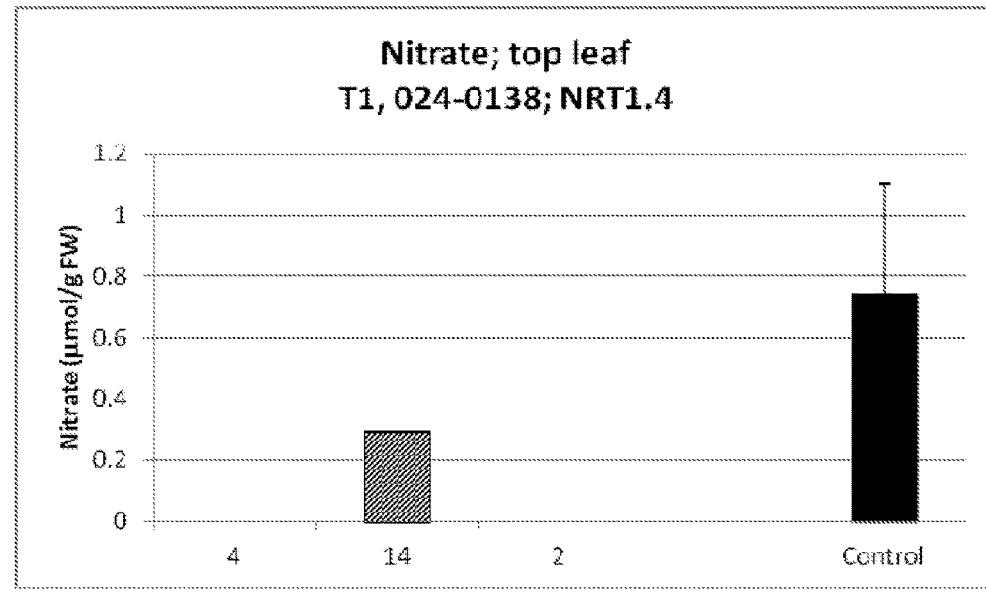
Figure 4B:
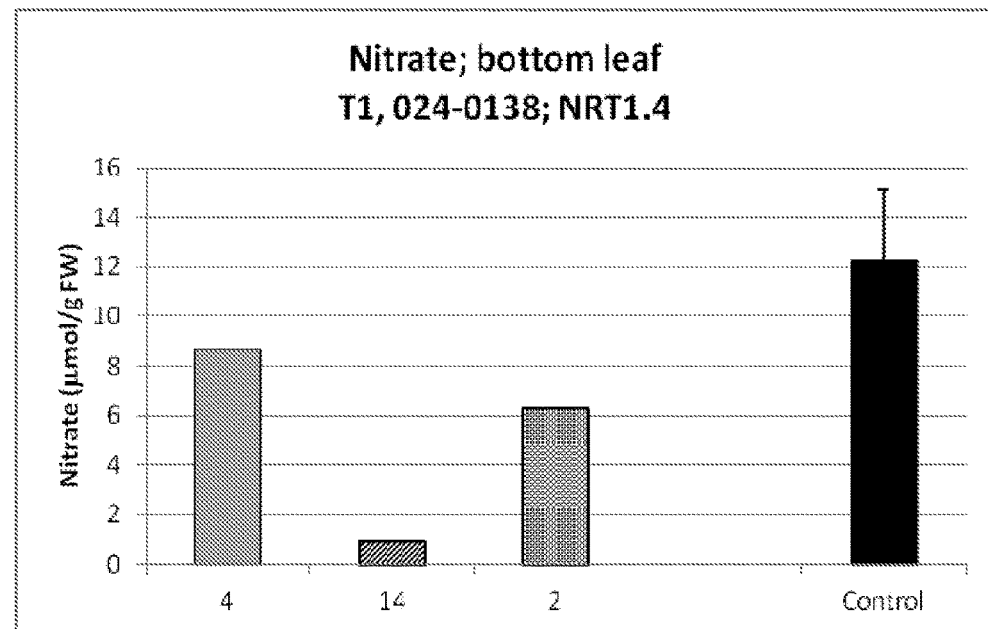
Figure 5A:
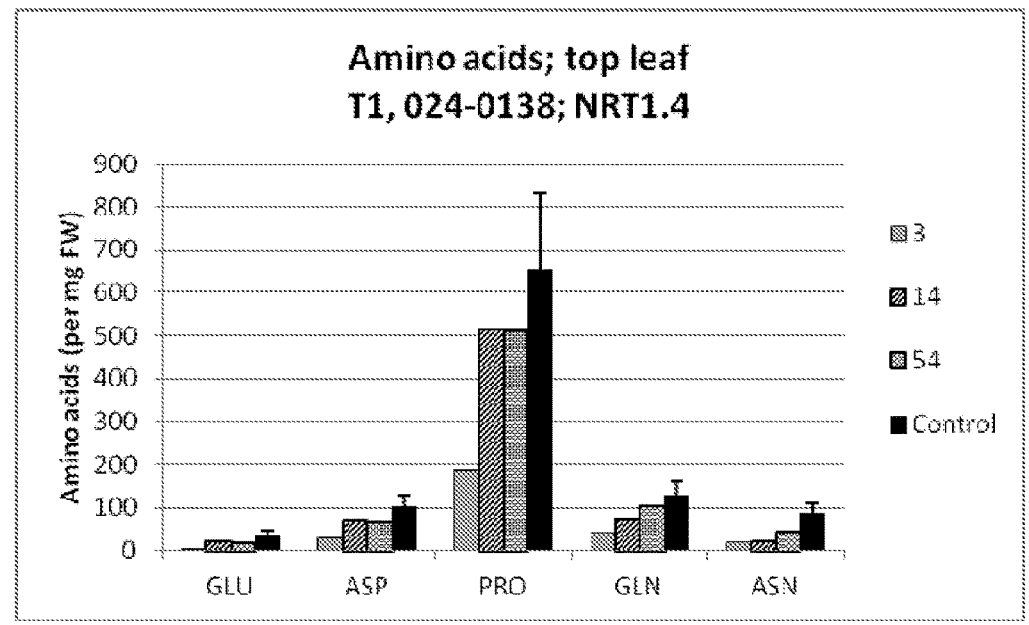
Figure 5B:
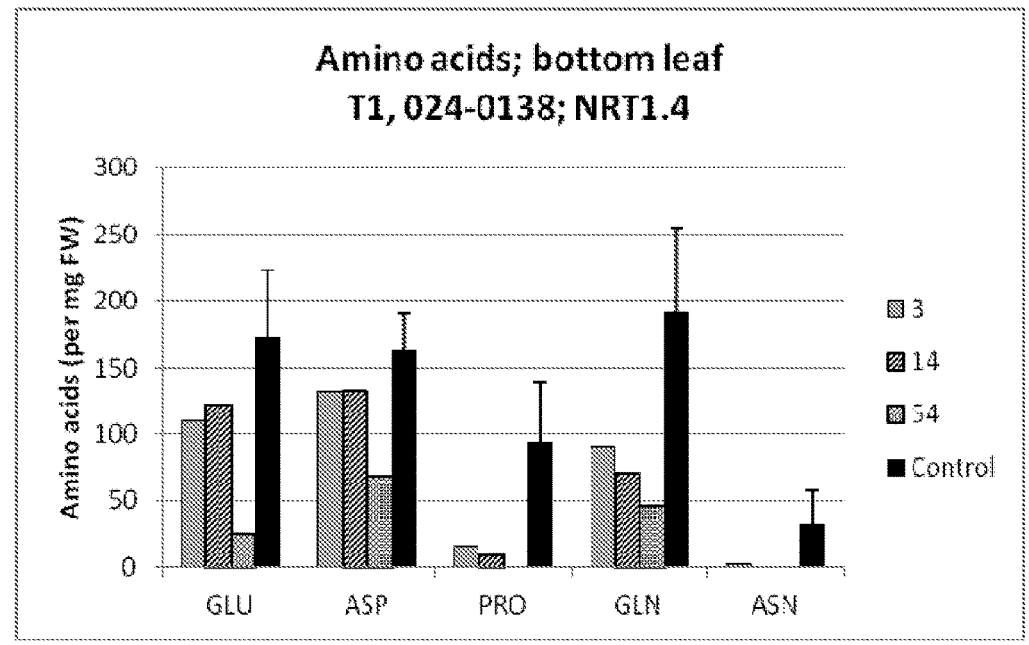
Figure 6A:
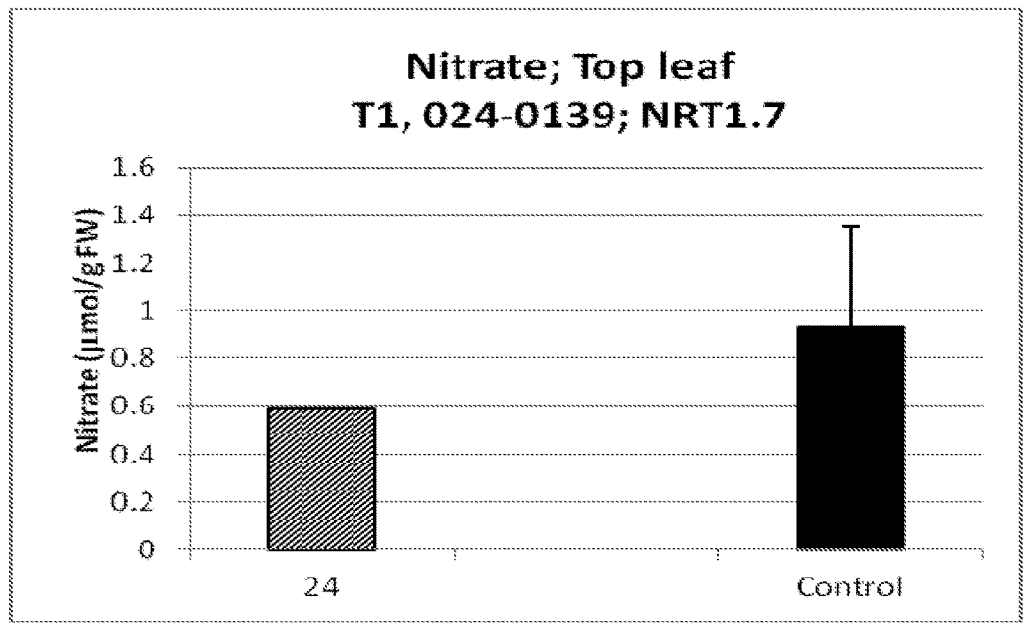
Figure 6B:
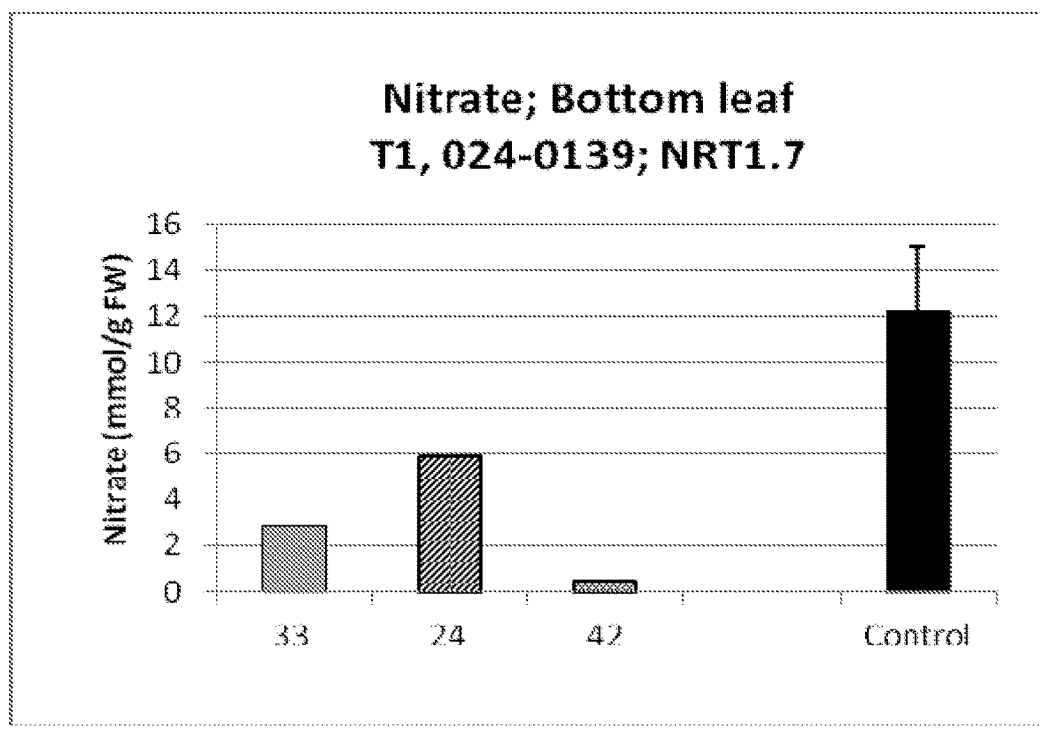
Figure 7A:
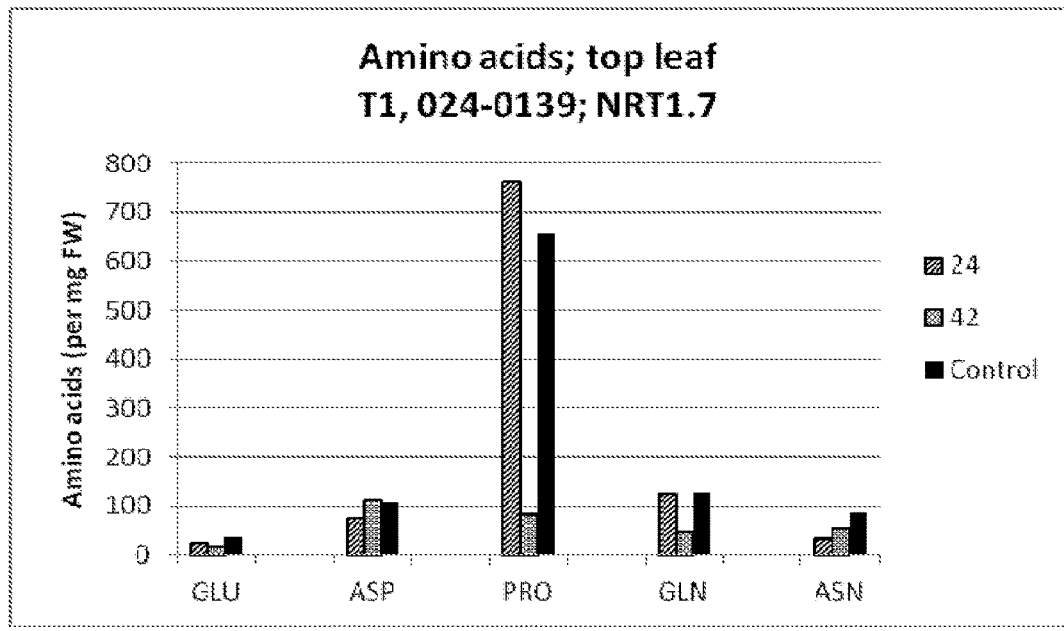
Figure 7B:
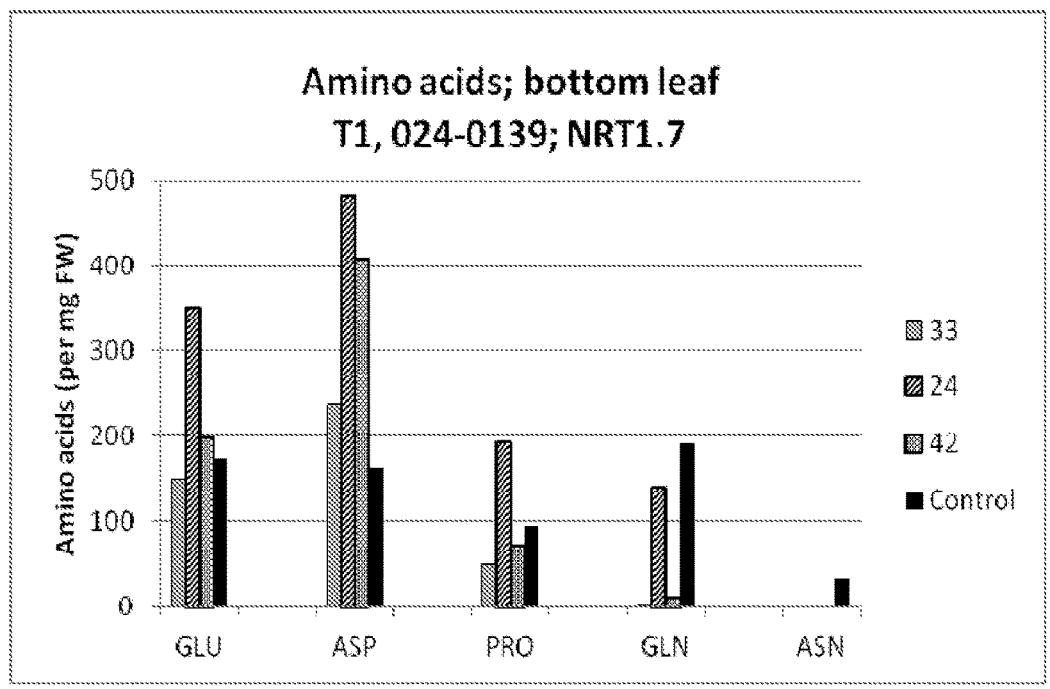
Figure 8A:
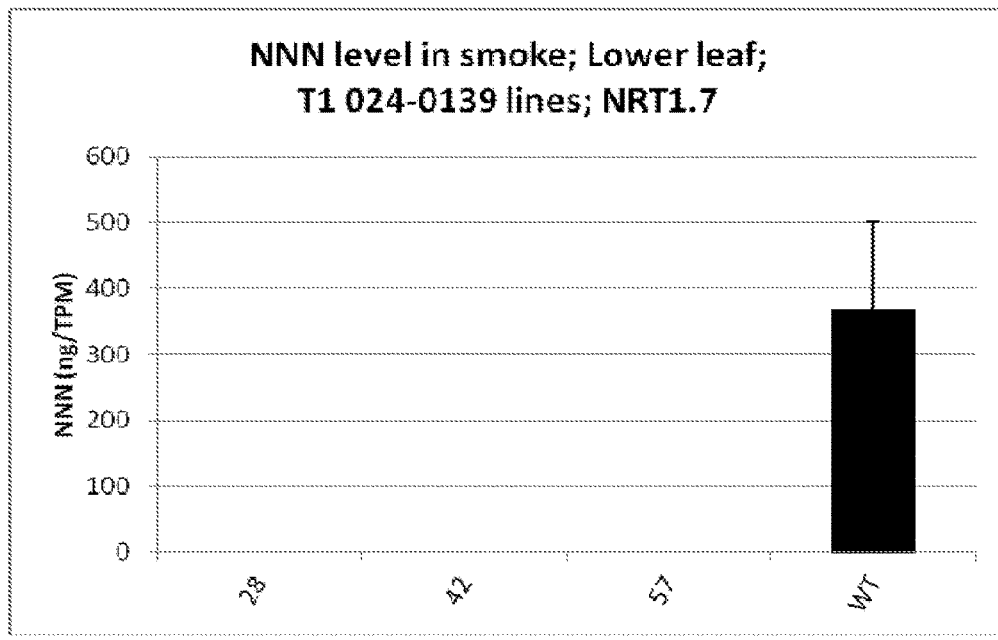
Figure 8B:
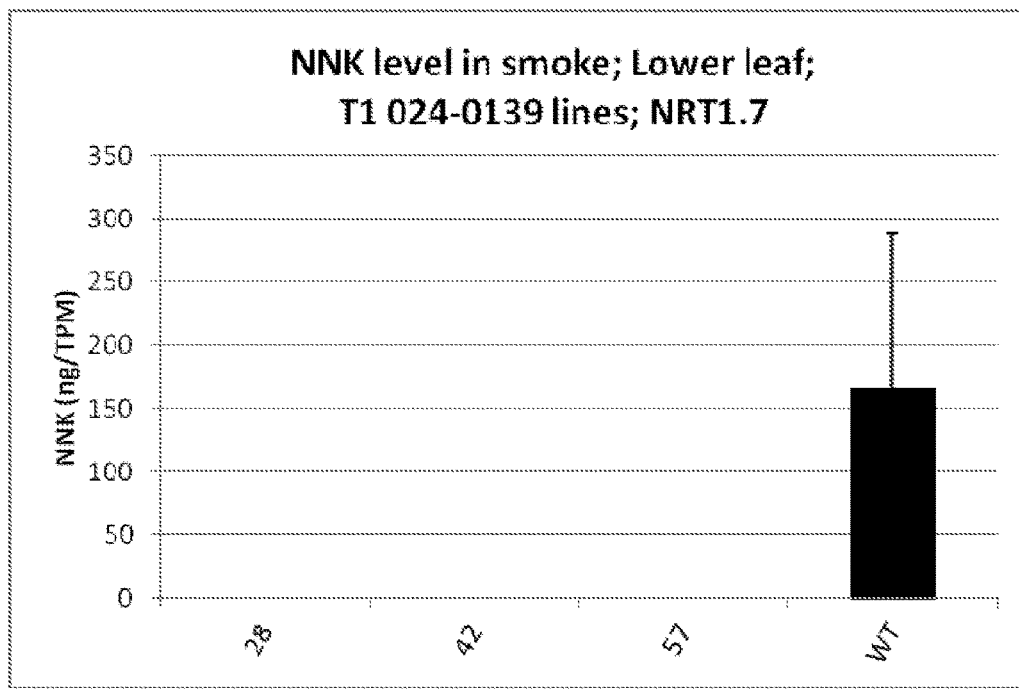

FIG. 1 shows the chemical structures of various tobacco smoke nitrosamines, 4-(Methylnitrosamino)-1-(3-pyridyl)-1-butanone (NNK), N-Nitrosonornicotine (NNN), N-Nitrosoanabasine (NAB) and N-Nitrosoanatabine (NAT);

FIG. 2a is a plasmid map of one embodiment of a construct according to the invention, known as pGNP024 0138 001. The construct includes the Atnr1.4 nitrate transporter gene under the control of the Carnation Etched Ring Virus (CERV) promoter, FIG. 2b is a plasmid map of a second embodiment of a construct according to the invention, known as pGNP024 0139 001. The construct includes the Atnrt1.7 nitrate transporter gene under the control of the Carnation Etched Ring Virus (CERV) promoter;

FIG. 3a shows the concentration of nitrate in the leaves of three T0 Burley PH2517 plant lines (i.e. 23, 29 and 33) harbouring the promoter CERV::NRT1.4 construct (Wild-type [WT] Burley PH2517 acted as control), FIG. 3b shows the concentration of nitrate in the leaves of three T0 Burley PH2517 plant lines (i.e. 53, 59 and 62) harbouring the promoter CERV::NRT1.7 construct (Wild-type [WT] Burley PH2517 acted as control);

FIG. 4a shows the concentration of nitrate in the top leaves of three T1 Burley PH2517 plant lines (i.e. 2, 4 and 14) harbouring the promoter CERV::NRT1.4 construct (Wild-type [WT] Burley PH2517 acted as control), FIG. 4b shows the concentration of nitrate in the bottom leaves of three T1 Burley PH2517 plant lines (i.e. 2, 4 and 14) harbouring the promoter CERV::NRT1.4 construct (Wild-type [WT] Burley PH2517 acted as control);

FIG. 5a shows the concentration of various amino acids (i.e. Glutamic Acid (Glu), Aspartic Acid (Asp), and Proline (Pro), Glutamine (Gln) and Asparagine (Asn), respectively) in the top leaves of three T1 Burley PH2517 plant lines (i.e. 3, 14 and 54) harbouring the promoter CERV::NRT1.4 construct (Wild-type [WT] Burley PH2517 acted as control), FIG. 5b shows the concentration of various amino acids (i.e. Glutamic Acid (Glu), Aspartic Acid (Asp), and Proline (Pro), Glutamine (Gln) and Asparagine (Asn), respectively) in the bottom leaves of three T1 Burley PH2517 plant lines (i.e. 3, 14 and 54) harbouring the promoter CERV::NRT1.4 construct (Wild-type [WT] Burley PH2517 acted as control);

FIG. 6a shows the concentration of nitrate in the top leaves of a T1 Burley PH2517 plant line (i.e. 24) harbouring the promoter CERV::NRT1.7 construct (Wild-type [WT] Burley PH2517 acted as control), FIG. 6b shows the concentration of nitrate in the bottom leaves of three T1 Burley PH2517 plant lines (i.e. 24, 33 and 42) harbouring the promoter CERV::NRT1.7 construct (Wild-type [WT] Burley PH2517 acted as control);

FIG. 7a shows the concentration of various amino acids (i.e. Glutamic Acid (Glu), Aspartic Acid (Asp), and Proline (Pro), Glutamine (Gln) and Asparagine (Asn), respectively)

in the top leaves of two T1 Burley PH2517 plant lines (i.e. 24 and 42) harbouring the promoter CERV::NRT1.7 construct (Wild-type [WT] Burley PH2517 acted as control), FIG. 7b shows the concentration of various amino acids (i.e. Glutamic Acid (Glu), Aspartic Acid (Asp), and Proline (Pro), Glutamine (Gln) and Asparagine (Asn), respectively) in the bottom leaves of three T1 Burley PH2517 plant lines (i.e. 24, 33 and 42) harbouring the promoter CERV::NRT1.7 construct (Wild-type [WT] Burley PH2517 acted as control); and FIG. 8a shows the concentration of N-Nitrosonornicotine (NNN) in smoke derived from the lower leaves of three T1 greenhouse-grown Burley tobacco lines (i.e. 28, 42 and 57) harbouring the promoter CERV::NRT1.7 construct (Wild type [WT] Burley PH2517 acted as control), FIG. 8b shows the concentration of 4-(Methylnitrosamino)-1-(3-pyridyl)-1-butanone (NNK) in smoke derived from the lower leaves of three T1 greenhouse-grown Burley tobacco lines (i.e. 28, 42 and 57) harbouring the promoter CERV::NRT1.7 construct (Wild type [WT] Burley PH2517 acted as control).

DETAILED DESCRIPTION & EXAMPLES

The inventors have developed two constructs, as shown in FIG. 2, and have used them to create six transgenic plant lines which over-express the *Arabidopsis thaliana* nitrate transporter genes nrt1.4 and nrt1.7 each under the control of the constitutive promoter, Carnation Etched Ring Virus (CERV) promoter (Hull et al., 1986, EMBO J., 5, 3083-3090).

Example 1—Isolation of *Arabidopsis thaliana* Nitrate Transporter Genes

The *Arabidopsis thaliana* nitrate transporter genes used in these experiments were Atnrt1.4 and Atnrt1.7.
Design of Primers
The full length genomic sequence coding for the *Arabidopsis thaliana* nitrate transporters Nrt1.4 and Nrt1.7 identified (Accession Number for the sequences were: Nrt1.4: AT2G26690 and Nrt1.7: AT1G69870). Primers for use in PCR to isolate the cDNA sequence were designed, which were tailed at the 5' end with a 4 bp spacer and attB sequences at the 5' and 3' end of the fragment to enable the cloning of the fragments into appropriate pDONR vector. It will be appreciated by the skilled person that other PCR primers could be designed incorporating the required features of the primers and alternative restriction enzyme sites.
Isolation of *Arabidopsis* cDNA Encoding Nrt1.4 and Nrt1.7

*Arabidopsis thaliana* var. *Columbia* RNA was extracted from the leaves of 3-week old plants using the Qiagen RNA Easy miniprep extraction kit (QIAGEN Ltd., Crawley, UK) and by following the manufacturer's instructions. This method provided sufficient amounts of RNA for gene isolation and cloning strategies. Following this, cDNA was created using the extracted RNA samples, Superscript Reverse Transcriptase (Invitrogen) and oligo dt primers according to the manufacturer's instructions. The cDNA was then purified using a Wizard clean up kit (Promega).
Isolation of Nrt1.4 Nitrate Transporter cDNA Fragments The cDNA sequence of *Arabidopsis* nrt1.4 is 1734 bp long (accession number: AT2G266900). cDNA encoding *Arabidopsis* Nrt1.4 was amplified with primer pairs SEQ ID NO.6 and SEQ ID NO.7, as shown below, which generated attB recombination sites at the 5' and 3' end and of the fragment.

```
Forward
                                         [SEQ ID NO. 6]
GGGGACAAGTTTGTACAAAAAAGCAGGCTYYATGGAGAGCAAAGGGAGT
TGGAC Reverse
                                         [SEQ ID NO. 7]
GGGGACCACTTTGTACAAGAAAGCTGGGTYTCAGCAGTCTTCAACTGAA
AATCC
```

PCR Conditions for *Arabidopsis* Nrt1.4
Cycle program: 1 cycle of 98° C. for 30 seconds, followed by 30 cycles of 98° C. for 10 seconds, 59° C. for 30 seconds and 72° C. for 2 minutes. This was then followed by 1 cycle of 72° C. for 10 minutes. Bands were isolated using Phusion polymerase (NE Biolabs) and by following the manufacturer's instructions.

An aliquot of the PCR reactions was then analysed by agarose gel electrophoresis. Reactions were precipitated and then stored. Nrt1.4 nitrate transporter DNA fragments were then cloned into pDONR™ zeo entry vectors (available from Invitrogen), as described below.
BP Recombination Reactions for *Arabidopsis* Nrt1.4

1 µl of the pDONR™ zeo vector (at 150 ng/l), 1.4 µl of the PCR reaction, 2 µl of BP clonase II enzyme mix were taken together with TE buffer. The mixture was then left at 25° C. for 2 hours. 1 µl of proteinase K was added to stop the reaction, which was then left at 37° C. for 10 minutes. 1 µl of the BP ligation reaction mixture was then added to 50 µl of TOP10 chemically competent *E. coli* cells. The mixture was then left on ice for 30 mins. The cells were then heat-shocked at 42° C. for 30 seconds, and then left on ice for a further 2 min. The cells were then placed in 250 µl of SOC media and incubated at 37° C. for 90 minutes. The cells were then plated onto agar plates containing 50 µg/ml zeocin and left overnight at 37° C. Cells containing plasmids grew into colonies, and approximately 30 colonies were observed for each gene sequence. Single colonies were picked and cultured in LB medium for each gene sequence. DNA mini preps (Qiagen) were made for each individual colony and a restriction digest, using HindIII, was used to determine if the gene had been incorporated into the pDONR vector. Colony PCR was used to select individual clones containing the pDONR vector with successfully inserted genomic DNA fragments.
Isolation of Nrt1.7 Nitrate Transporter cDNA Fragments The cDNA sequence of *Arabidopsis* nrt1.7 is 1863 bp long (accession number: At1G69870). cDNA encoding *Arabidopsis* Nrt1.7 was amplified with primer pairs SEQ ID NO.8 and SEQ ID NO.9, as shown below, which also generated attB sequences at the 5' and 3' end of the fragment.

```
Forward
                                         [SEQ ID NO. 8]
ATCGGTACCATGGTTTTGGAGGATAGAAAGGACGGT Reverse
                                         [SEQ ID NO. 9]
AGCGAGCTCTCATTTCATCGATTTCTTCGAAGTCAT
```

An aliquot of the PCR reactions were then analysed by agarose gel electrophoresis. Reactions were precipitated and then stored. Nrt1.7 nitrate transporter DNA fragments were then cloned into pDONR™ zeo entry vectors (available from Invitrogen), as described below.
PCR Conditions for *Arabidopsis* Nrt1.7
Cycle program: 1 cycle of 98° C. for 30 seconds, followed by 30 cycles of 98° C. for 10 seconds, 59° C. for 30 seconds and 72° C. for 2 minutes. This was followed by 1 cycle of 72° C. for 10 minutes. Bands were isolated using Phusion polymerase (NE Biolabs) and by following manufacturer's instructions.

An aliquot of the PCR reactions were then analysed by agarose gel electrophoresis. Reactions were precipitated and then stored. Nrt1.7 nitrate transporter DNA fragments were then cloned into pDONR™ zeo entry vectors (available from Invitrogen), as described below.

BP Recombination Reactions for *Arabidopsis* nrt1.7

1 µl pDONR™ zeo entry vector (at 150 ng/µl), 1.4 µl PCR reaction and 2 µl of BP clonase II enzyme mix were mixed together with TE buffer. The mixture was left at 25° C. for 2 hours. 1 µl of proteinase K was added to stop the reaction, which was then left at 37° C. for 10 minutes. 1 µl of the BP ligation reaction mixture was then added to 50 µl of TOP10 chemically competent *E. coli* cells. The mixture was then left on ice for 30 mins. The cells were then heat-shocked at 42° C. for 30 seconds, and then left on ice for a further 2 min. The cells were then placed in 250 µl of SOC media and incubated at 37° C. for 90 minutes. The cells were then plated onto agar plates containing 50 µg/ml zeocin and left overnight at 37° C. Cells containing plasmids grew into colonies, and approximately 30 colonies were observed for each gene sequence. Single colonies were picked and cultured in LB medium for each gene sequence. DNA mini preps (Qiagen) were made for each individual colony and a restriction digest, using HindIII, was used to determine if the gene had been incorporated into the pDONR vector. Colony PCR was used to select individual clones containing the pDONR vector with successfully inserted genomic DNA fragments.

Sequence Analysis

Colonies that contained the vector were sent to Lark Technologies for sequencing using to the primer pairs M13F and M13R (as shown in SEQ ID No. 10 and 11 below). Sequence alignments were performed using Vector NTi programs. Analysis of their sequences showed that the clones contained the nitrate transporter genes nrt1.4 and nrt1.7.

```
MI3F (Forward)
                                      [SEQ ID NO. 10]
GTGT AAA ACG ACG GCC AGT MI3R (Reverse)
                                      [SEQ ID NO. 11]
AGG AAA CAG CTA TGA CCA T
```

Example 2—Construction of Vectors for Tobacco Transformation Using the LR Recombination Reaction Cloning of cDNA Encoding Atnrt 1.4 and Atnrt1.7 into a Gateway Converted Binary (Destination) Vector pDONR™ zeo plasmids containing either the nrt1.4 or nrt1.7 gene were recombined in a LR recombination reaction: 1 µl (215 ng/µl Nrt1.4) or (218 ng/µl Nrt1.7), 1 µl pBNP CERV (39 ng/µl), TE buffer and 2 µl LR clonase II were incubated at 25° C. for 90 minutes. 1 µl proteinase K was then added to stop the reaction, which was then incubated at 37° C. for 15 minutes. The transformed vector was subsequently used to transform *E. coli* chemically TOP10 cells.

The pBNP vector is an in-house vector created from the pBNP binary vector (van Engelen et al., 1995, Transgenic Research, 4:288-290), containing the CERV promoter and the nopaline synthase terminator. It was converted into a Gateway ready vector by the addition of the Gateway conversion cassette (Invitrogen) following manufacturer's instructions. Cells containing the plasmid were selected on kanamycin plates. Clones were then isolated and the DNA was extracted and analysed by restriction digestion followed by sequencing.

The CERV promoter is a constitutive promoter of the caulimovirus group of plant viruses. It was isolated and characterised in 1986 by Hull et al. and is characteristic of CaMV (Hull et al., 1986), but has little sequence similarity with the CaMV 35S promoter.

The following binary vectors were produced:—
(i) pGNP024 0138 001 (see FIG. 2a): Carnation Etched Ring Virus (CERV) promoter: N rt1.4 eDNA: Nos terminator; and
(ii) pGNP024 0139 001 (see FIG. 2b): Carnation Etched Ring Virus (CERV) promoter: Nrt1.7 eDNA: Nos terminator.

The binary vector was then transformed into *Agrobacterium tumefaciens* LBA 4404 by electroporation. This was performed by mixing 40 µl of *A. tumefaciens* electrocompetent cells and 0.5 µg of plasmid DNA, and placing in a pre-cooled cuvette. The cells were then electroporated at 1.5 Volts, 600 Ohms and 25 µFD. 1 ml of 2YT media was added to the cuvette and the mixture was decanted into a 30 ml universal container and incubated at 28° C. for 2 hours in a shaking incubator. 100 µl of cells were then plated onto kanamycin (50 µg/ml) and streptomycin (100 µg/ml) LB agar plates. The plates were left to incubate for 2 days at 28° C.

Example 3—Transformation of Tobacco

Burley PH2517 were transformed with both pGNP024 0138 001 and pGNP024 0139 001 using the method of leaf disk co-cultivation, as described by Horsch et al. (Science 227: 1229-1231, 1985). The youngest two expanded leaves were taken from 7-week old tobacco plants and were surface-sterilised in 8% Domestos for 10 minutes and washed 3 times with sterile distilled water. Leaf disks were then cut using a number 6 cork borer and placed in the transformed *Agrobacterium* suspension for approximately two minutes. The discs were then gently blotted between two sheets of sterile filter paper. 10 disks were placed on MS media 3% sucrose+2.2 µM BAP+0.27 µM NAA plates, which were then incubated for 2 days in the growth room. Discs were then transferred to plates of MS media+3% sucrose+2.2 µM BAP+0.27 µM NAA supplemented with 500 g/l Cefotaxime and 100 g/l kanamycin. After 2 weeks, the discs were transferred onto fresh plates of the above medium. After a further two weeks the leaf disks were transferred onto plates containing LS media+3% sucrose+0.5 µM BAP supplemented with 500 mg/l Cefotaxime and 100 mg/l kanamycin. The leaf disks were transferred onto fresh medium every two weeks. The shoots were excised as they appeared and transferred to jars of LS media+3% sucrose+0.5 µM BAP supplemented with 500 mg/l Cefotaxime. The shoots were transferred, in jars, to LS media+3% sucrose+250 mg/l Cefotaxime after approximately 3 weeks. After a further 3-4 weeks, the plants were finally transferred to LS+3% sucrose (no antibiotics) and rooted. Once the plants were rooted they were transferred to soil in the greenhouse.

Example 4—Analysis of Tobacco Leaf Nitrate Content (T0 Plants)

Quantification of nitrate and/or nitrite levels in wild-type and transgenic Burley PH2517 plants was performed using HPLC. This method for determining nitrate concentrations in plant tissues is described in Sharma et al., 2008 (Malaria Journal, 7: pp 71). HPLC provides highly accurate measurements of nitrate and/or nitrite levels from plant samples and also reduces the concerns associated with handling hazardous agents due to the increased level of automation associated with the methodology.

Materials are:
Running Buffer: 5 mM $K_2HPO_4$, 25 mM $KH_2PO_4$ at pH3
Extraction Buffer: 5 mM $K_2HPO_4$, 25 mM $KH_2PO_4$ at pH3
Method: Firstly, 2 ml of the phosphate buffer is added to 250-300 mg of ground leaf material and homogenised in mortar with a pestle. These ratios can be modified according to the expected level of nitrate. The homogenate is then centrifuged at 16000 rpm at +4° C. for 10 minutes. 1 ml of the supernatant is then filtered through a syringe filter (0.2 µm) into an HPLC vial. Nitrate and Nitrite standard curves were constructed with concentrations range of 0-1 mM for nitrate and 0 to 100 µM for nitrite. The injection volume is 20 µl.

The peak identification is done according to peak timing. Peak timing is variable depending on column age and a number of other factors. Thus standards should be used to assess peak position and related this to peak run off time in samples.

The nitrate results illustrated in FIG. 3A show that there is a lowering of leaf nitrate concentration in the transformed plants with the CRV-AtNrt1.4 construct of the invention. Although they do not wish to be bound by theory, the inventors hypothesise that the AtNrt1.4 protein is acting as a nitrogen remobiliser. This results in the leaves being depleted of nitrate.

The nitrate results illustrated in FIG. 3B show that there is a lowering of leaf nitrate concentration in the transformed plants with the CRV-AtNrt1.7 construct of the invention. Although they do not wish to be bound by theory, the inventors hypothesise that the AtNrt1.7 protein is acting as a nitrogen remobiliser. This results in the leaves being depleted of nitrate.

Example 5—Analysis of Tobacco "Upper" and "Lower" Leaf Nitrate Content (T1 Plants)

Method: Quantification of nitrate and/or nitrite levels in wild-type and transgenic Burley PH2517 plants was performed using the method described in Example 4.

FIGS. 4 and 6 show that the upper and lower leaves of the three (T1) test plant lines over-expressing either the Atnrt1.4 nitrate transporter or the Atnrt1.7 nitrate transporter, possess a reduced nitrate content, compared to the corresponding leaves of their wild-type counterpart. Therefore, this suggests that within the upper and lower leaves of the test plant, the nitrate content has been reduced by over-expression of either CRV-AtNrt1.4 or AtNrt1.7.

Although not wishing to be bound by following theory, the inventors hypothesise that the AtNrt1.4 and AtNrt1.7 proteins act as nitrogen remobilisers, which cause a reduction in the nitrate content of leaves.

Example 6—Analysis of Tobacco "Upper" and "Lower" Leaves Amino Acid Content (T1 Plants)

The physiology of a leaf is dependent on its position in relation to the rest of the plant. Therefore, tobacco growers must bear this information in mind when considering what flavour a leaf may possess.

During flowering, a process called remobilization occurs, which results in the transport of nutrients, such as amino acids and nitrogenous compounds, out from the base of the plant towards the top of the plant. In addition, remobilized nutrients will be used as an energy source for seed production. Therefore, lower and upper leaves will have a different nitrogen content illustrated by a different amino acid profile.

In view of the above, the amino acid content of wild-type and transgenic Burley PH2517 plants were determined using the EZ: Faast LC/MS kit supplied by Phenomenex. All the reagents and the supplies, including the HPLC column, are components of the kit.

All the steps of the procedure are provided in the User's manuals KH0-7338 which are used as a protocol.

Method: In principle, it involves solid phase extraction of the samples to be analysed, followed by a derivatization and a liquid/liquid extraction. The derivatized samples were analyzed quickly by liquid chromatography-mass spectrometry (LC-MS).

The solid phase extraction was performed via a sorbent packed tip that binds amino acids while allowing interfering compounds to flow through. Amino acids which were bound to the sorbent were then extruded into the sample vial and quickly derivatized with reagent at room temperature in aqueous solution. Derivatized amino acids concomitantly migrated to the organic layer for additional separation from interfering compounds. The organic layer was then removed, evaporated and re-dissolved in aqueous mobile phase and analyzed on a LC-MS system.

FIGS. 5 and 7 summarise the effect of Atnrt1.4 and Atnrt1.7 nitrate transporter over-expression on the concentration of Glu, Asp, Pro, Gln and Asn (i.e. amino acids believed to be involved in the nitrogen assimilation pathway of plants) in multiple plant lines. Both figures clearly show that upper leaves of plants harbouring either the Atnrt1.4 or Atnrt1.7 nitrate transporter construct exhibit a significant reduction (compared to the upper leaves of their wild-type counterpart) in the concentration of all the amino acids measured. This result was also achieved in the lower leaves of plants that over-expressed the Atnrt1.4 nitrate transporter (see FIG. 5b).

However, conversely, in the lower leaves of plants the over-expressed the Atnrt1.7 nitrate transporter, an increase in the concentration of the amino acids, Glu, Asp and Pro, was observed (see FIG. 7b).

Example 7—Analysis of N-Nitrosonornicotine (NNN) and 4-(Methylnitrosamino)-1-(3-pyridyl)-1-butanone (NNK) and Tobacco-Specific Nitrosamine (TSNA) in Smoke Derived from the Lower Leaves Burley Tobacco Lines In view of the reduced nitrate content of the test plant leaves, as shown in Examples 4 and 5, and the reduced amino acid content of test plant leaves, as shown in Example 6, the inventors decided to determine whether these reductions correspond with a reduction in NNN and NNK formation by smoke derived from the leaves of plants that over-express the CRV-AtNrt1.7 construct.

As clearly shown by FIG. 8, the NNN and NNK content within smoke derived from the lower leaves of the plants lines, 28, 42 and 57, which over-express the CRV-AtNrt1.7 construct, is significantly lower than the NNN and NNK content of smoke derived from the lower leaves of wild-type plants grown under the same conditions.

In addition, the inventors also found that over-expression of the CRV-ArNrt1.7 construct in Burley tobacco plants also caused a significant reduction (below the limit of detection)

in the TSNA content of smoke derived from the lower leaves of Burley tobacco plants (compared to the level of TSNA found within smoke derived from the lower leaves of wild-type plants grown under the same conditions) (data not shown).

These results clearly show that over-expression of the genetic constructs according to the invention may be advantageous for tobacco plants. Furthermore, manipulation of the amino acid profiles can be used to modify the flavour of tobacco.

The invention claimed is:

1. A method of decreasing nitrate concentration in leaves of a test plant to below that of the corresponding nitrate concentration in leaves of a wild-type plant cultured under the same conditions, the method comprising:

(i) transforming a plant cell of the test plant with a genetic construct comprising a promoter operably linked to a coding sequence encoding a polypeptide having nitrate transporter activity or a vector comprising said genetic construct, wherein a) the polypeptide comprises an amino acid sequence as set out in SEQ ID No.2, or an amino acid sequence of a functional variant which has at least 97% sequence identity therewith, or b) the coding sequence comprises a nucleic acid sequence as set out in SEQ ID No.1, or a polynucleotide sequence of a functional variant which has at least 97% sequence identity therewith, and further wherein the promoter is a Carnation Etched Ring Virus (CERV) promoter; and (ii) regenerating a plant from the transformed cell, wherein the regenerated transformed plant expresses the nitrate transporter from the genetic construct and has decreased nitrate concentration in its leaves when compared to the wild-type plant.

2. A method of producing a transgenic plant which transports nitrate out of a leaf at a higher rate than a corresponding wild-type plant cultured under the same conditions, the method comprising:

(i) transforming a plant cell of the test plant with a genetic construct comprising a promoter operably linked to a coding sequence encoding a polypeptide having nitrate transporter activity or a vector comprising said genetic construct, wherein a) the polypeptide comprises an amino acid sequence as set out in SEQ ID No.2, or an amino acid sequence of a functional variant which has at least 97% sequence identity therewith, or b) the coding sequence comprises a nucleic acid sequence as set out in SEQ ID No. 1, or a polynucleotide sequence of a functional variant which has at least 97% sequence identity therewith, and further wherein the promoter is a Carnation Etched Ring Virus (CERV) promoter; and (ii) regenerating a plant from the transformed cell, wherein the regenerated transformed plant expresses the nitrate transporter from the genetic construct and has decreased nitrate concentration in its leaves when compared to the wild-type plant.

3. The method according to claim 1, wherein the coding sequence is from *Arabidopsis* spp.

4. The method according to claim 1, wherein the coding sequence is from *Arabidopsis thaliana.*

5. The method of claim 1, wherein said CERV promoter comprises SEQ ID No. 5.

6. The method of claim 1, wherein said polypeptide comprises a sequence having at least 97% identity to the full length of SEQ ID NO: 2 and said polynucleotide has at least 97% identity to the full length of SEQ ID NO: 1.

7. The method of claim 1, where said polynucleotide comprises SEQ ID NO: 2 and said nucleic acid sequence comprises SEQ ID NO: 1.

8. The method of claim 7, wherein said CERV promoter comprises SEQ ID NO: 5.

* * * * *

SEQUENCE LISTING

```
<160> NUMBER OF SEQ ID NOS: 11

<210> SEQ ID NO 1
<211> LENGTH: 1734
<212> TYPE: DNA
<213> ORGANISM: Arabidopsis thaliana

<400> SEQUENCE: 1
atggagagca aagggagttg gacagtggct gatgccgtag actacaaagg acgacctgcc       60
gacaaatcca aaaccggtgg ttggatcact gccgctctca ttcttgggat agaagttgtg      120
gagaggctat caacaatggg aatagcagtg aatttggtaa catatttgat ggagacaatg      180
catctcccaa gttcaacctc tgccaacatt gtcactgatt tcatgggcac ttccttcctc      240
ctatgcttgc tcggtggttt tctcgctgac tccttcctcg gccgtttcaa aaccatcggc      300
attttctcaa ccattcaagc tctgggaact ggtgctctag cggtagcaac taagctgcca      360
gagctacgtc caccaacatg ccatcatgga gaagcttgca tacccgcgac cgccttccaa      420
atgacaattc tttatgtttc gctttacctt atagcccttg aactggtgg tcttaaatct       480 agtatctctg gatttgggtc tgaccagttt gatgacaaag atcctaaaga gaaagctcac      540
atggctttct tcttcaacag gttcttcttc tttattagta tggggacatt attggctgtg      600
actgttttag tttacatgca agatgaagtg ggaagatctt gggcttatgg aatctgcact      660
gtctctatgg ctatagctat tgtaatattc ttgtgtggga ctaagagata ccgttataag      720
aagagccaag gaagtcccgt tgtgcaaata tttcaggtca tagcagctgc gttccgaaag      780
aggaaaatgg aactacctca aagcattgtt tatctttatg aagataaccc tgaaggcatt      840
agaattgaac atactgatca gtttcacttg ttggacaagg cggccatagt tgcagaagga      900
gattttgaac aaacccttga tggagttgca atcccaaacc cttggaagct aagctcagtg      960
accaaagttg aggaagtaaa aatgatggtt aggcttttgc ctatttgggc aacaactata     1020
attttttgga caacatatgc ccaaatgatt acattctctg ttgagcaagc ttcaactatg     1080
agacgtaaca ttggaagctt taagatccca gctggttccc tcaccgtgtt tttcgttgcg     1140
gctattctca taactctagc tgtctacgac cgtgccataa tgccttttg gaagaaatgg      1200 aaaggaaaac caggtttctc tagcctacaa agaatagcta ttggattggt cttatcaacc     1260
gctggaatgg cagctgcagc tctagtagag caaaagcgtt tatccgttgc gaaatctagt     1320
tcacaaaaaa cattgcctat aagtgtgttt ttacttgttc cacaattctt cttagtagga     1380
gctggggaag ccttttatcta cactggccaa cttgatttct tcataacaca atcgcctaag     1440
ggaatgaaaa ctatgagcac tggactcttc ttgaccactt tatcactagg tttctttgtc     1500
agcagtttct tggtctcaat cgtcaagagg gtcacttcaa cttctactga tgtaggatgg     1560
ctggctgata acattaacca cggccgactc gattactttt attggctttt agtcattctc     1620
agtggaatta acttcgttgt ctatatcata tgtgccttgt ggtttaagcc aacgaagggt     1680
aaagactcag tagagaagga aaatggcaag ggattttcag ttgaagactg ctga          1734

<210> SEQ ID NO 2
<211> LENGTH: 577
```

```
<212> TYPE: PRT
<213> ORGANISM: Arabidopsis thaliana

<400> SEQUENCE: 2

Met Glu Ser Lys Gly Ser Trp Thr Val Ala Asp Ala Val Asp Tyr Lys
1               5                   10                  15

Gly Arg Pro Ala Asp Lys Ser Lys Thr Gly Gly Trp Ile Thr Ala Ala
            20                  25                  30

Leu Ile Leu Gly Ile Glu Val Val Glu Arg Leu Ser Thr Met Gly Ile
        35                  40                  45

Ala Val Asn Leu Val Thr Tyr Leu Met Glu Thr Met His Leu Pro Ser
    50                  55                  60

Ser Thr Ser Ala Asn Ile Val Thr Asp Phe Met Gly Thr Ser Phe Leu
65                  70                  75                  80

Leu Cys Leu Leu Gly Gly Phe Leu Ala Asp Ser Phe Leu Gly Arg Phe
                85                  90                  95

Lys Thr Ile Gly Ile Phe Ser Thr Ile Gln Ala Leu Gly Thr Gly Ala
            100                 105                 110

Leu Ala Val Ala Thr Lys Leu Pro Glu Leu Arg Pro Pro Thr Cys His
        115                 120                 125

His Gly Glu Ala Cys Ile Pro Ala Thr Ala Phe Gln Met Thr Ile Leu
    130                 135                 140

Tyr Val Ser Leu Tyr Leu Ile Ala Leu Gly Thr Gly Gly Leu Lys Ser
145                 150                 155                 160

Ser Ile Ser Gly Phe Gly Ser Asp Gln Phe Asp Asp Lys Asp Pro Lys
                165                 170                 175

Glu Lys Ala His Met Ala Phe Phe Phe Asn Arg Phe Phe Phe Phe Ile
            180                 185                 190

Ser Met Gly Thr Leu Leu Ala Val Thr Val Leu Val Tyr Met Gln Asp
        195                 200                 205

Glu Val Gly Arg Ser Trp Ala Tyr Gly Ile Cys Thr Val Ser Met Ala
    210                 215                 220

Ile Ala Ile Val Ile Phe Leu Cys Gly Thr Lys Arg Tyr Arg Tyr Lys
225                 230                 235                 240

Lys Ser Gln Gly Ser Pro Val Val Gln Ile Phe Gln Val Ile Ala Ala
                245                 250                 255

Ala Phe Arg Lys Arg Lys Met Glu Leu Pro Gln Ser Ile Val Tyr Leu
            260                 265                 270

Tyr Glu Asp Asn Pro Glu Gly Ile Arg Ile Glu His Thr Asp Gln Phe
        275                 280                 285

His Leu Leu Asp Lys Ala Ala Ile Val Ala Glu Gly Asp Phe Glu Gln
    290                 295                 300

Thr Leu Asp Gly Val Ala Ile Pro Asn Pro Trp Lys Leu Ser Ser Val
305                 310                 315                 320

Thr Lys Val Glu Glu Val Lys Met Met Val Arg Leu Leu Pro Ile Trp
                325                 330                 335

Ala Thr Thr Ile Ile Phe Trp Thr Thr Tyr Ala Gln Met Ile Thr Phe
            340                 345                 350

Ser Val Glu Gln Ala Ser Thr Met Arg Arg Asn Ile Gly Ser Phe Lys
        355                 360                 365

Ile Pro Ala Gly Ser Leu Thr Val Phe Phe Val Ala Ala Ile Leu Ile
    370                 375                 380

Thr Leu Ala Val Tyr Asp Arg Ala Ile Met Pro Phe Trp Lys Lys Trp
385                 390                 395                 400
```

Lys Gly Lys Pro Gly Phe Ser Ser Leu Gln Arg Ile Ala Ile Gly Leu
              405                 410                 415

Val Leu Ser Thr Ala Gly Met Ala Ala Ala Leu Val Glu Gln Lys
          420                 425                 430

Arg Leu Ser Val Ala Lys Ser Ser Gln Lys Thr Leu Pro Ile Ser
          435                 440                 445

Val Phe Leu Leu Val Pro Gln Phe Phe Leu Val Gly Ala Gly Glu Ala
450                 455                 460

Phe Ile Tyr Thr Gly Gln Leu Asp Phe Phe Ile Thr Gln Ser Pro Lys
465                 470                 475                 480

Gly Met Lys Thr Met Ser Thr Gly Leu Phe Leu Thr Thr Leu Ser Leu
              485                 490                 495

Gly Phe Phe Val Ser Ser Phe Leu Val Ser Ile Val Lys Arg Val Thr
              500                 505                 510

Ser Thr Ser Thr Asp Val Gly Trp Leu Ala Asp Asn Ile Asn His Gly
              515                 520                 525

Arg Leu Asp Tyr Phe Tyr Trp Leu Leu Val Ile Leu Ser Gly Ile Asn
          530                 535                 540

Phe Val Val Tyr Ile Ile Cys Ala Leu Trp Phe Lys Pro Thr Lys Gly
545                 550                 555                 560

Lys Asp Ser Val Glu Lys Glu Asn Gly Lys Gly Phe Ser Val Glu Asp
              565                 570                 575

Cys

<210> SEQ ID NO 3
<211> LENGTH: 1863
<212> TYPE: DNA
<213> ORGANISM: Arabidopsis thaliana

<400> SEQUENCE: 3

```
atggttttgg aggatagaaa ggacggttct tctttgccgg acgatccgg tagtttctct      60
aaatcgtcac cgtcggagtt ggatgttgtt gatccctaca agcggataag ttcgccggga     120
tctatattgg atgctgagaa ggtagagaaa aagcctggag gatggagagc cgtctcgttc     180
attttaggaa atgagacgct ggagagactg ggatcgatag gattgttggc aaacttcatg     240
gtttatctaa ccaaagtgtt tcacttagaa caagtcgacg ctgcaaatgt catcaacatt     300
tggtcaggtt tcaccaatct cactcctctc gtcggagcgt atatctcaga cacttatgtt     360
ggccgcttca agaccatcgc tttcgcctca ttcgccactc cctcggact aataacaatt     420
acactcacag catcgtttcc tcaactccac ccagcatcat gcaacagcca ggacccactc     480
agttgcggcg gtccgaataa gctccagatc ggagttttgc tattgggact ctgtttcctc     540
tccgtaggga gtgaggaat acgaccttgt agcatccctt tgggggttga tcagtttgac     600
caacgaactg aggaagggt taaggagtg gccagtttct tcaactgta ttacatgact      660
ttcactgtgg ttctgatcat tacacagacc gtagttgtgt atatccagga tcaagtcagt     720
tggattatcg gttttagtat ccctaccgga ctcatggctc ttgcggttgt tatgtttttt     780
gccggaatga agcgttatgt ctacgttaaa ccagaaggaa gtatattctc tgggatcgct     840
caagttatcg tggcagctcg taagaagcga aagctgaaac ttccggcgga agatgacggc     900
actgtcacct attacgaccc agccatcaag tctagcgtgt tatccaagtt acaccgcagt     960
aaccaattca ggtgtcttga caaagccgcg gtggttatag aaggtgacct aacacccgag    1020
ggacctcccg cagacaagtg gcggttatgc agcgtccaag aagtggaaga agtgaagtgt    1080
```

```
ttgatccgaa ttgttcctat ctggtcggcc ggaataatct cactcgcggc catgacaaca    1140
caaggcactt tcacggtctc tcaagctttg aaaatggatc gaaacttagg tcctaaattc    1200
gagattccgg ctggttcact ctccgtcatc tctctcctca caatcggcat ctttcttccc    1260
ttctacgacc gcgttttgt accattcatg cggcgaatca ccggccataa atccggaatc     1320
acactcctcc aaaggatagg aacagggatc gttttcgcga tcttttctat gatcgttgcg    1380
ggcattgtgg agcgtatgag acgcatacgc tccatcaatg ccggagatcc aacgggaatg    1440
actccaatgt cggtgttttg gctttcgccg cagctaattc tcatgggact atgtgaagca    1500
ttcaatatca tcggacaaat tgagttcttc aacagtcagt ttccagagca catgagaagt    1560
atcgctaact ctctcttctc tttatcgttc gccggttcga gctaccttag tagtttcctt    1620
gtgactgtcg ttcataaatt ctccggtggg catgatcgtc cggattggct aaacaagaat    1680
ctcaacgcgg gaaaattgga ttacttctat tatctgattg cggttttggg tgtggttaat    1740
ctggtttact tttggtattg tgctcgggga taccggtaca aggtcggttt accgattgaa    1800
gactttgagg aggacaagtc ctccgatgat gttgagatga cttcgaagaa atcgatgaaa    1860
tga                                                                  1863

<210> SEQ ID NO 4
<211> LENGTH: 620
<212> TYPE: PRT
<213> ORGANISM: Arabidopsis thaliana

<400> SEQUENCE: 4

Met Val Leu Glu Asp Arg Lys Asp Gly Ser Ser Leu Pro Gly Arg Ser
1               5                   10                  15

Gly Ser Phe Ser Lys Ser Ser Pro Ser Glu Leu Asp Val Val Asp Pro
            20                  25                  30

Tyr Lys Arg Ile Ser Ser Pro Gly Ser Ile Leu Asp Ala Glu Lys Val
        35                  40                  45

Glu Lys Lys Pro Gly Gly Trp Arg Ala Val Ser Phe Ile Leu Gly Asn
    50                  55                  60

Glu Thr Leu Glu Arg Leu Gly Ser Ile Gly Leu Ala Asn Phe Met
65                  70                  75                  80

Val Tyr Leu Thr Lys Val Phe His Leu Glu Gln Val Asp Ala Ala Asn
                85                  90                  95

Val Ile Asn Ile Trp Ser Gly Phe Thr Asn Leu Thr Pro Leu Val Gly
            100                 105                 110

Ala Tyr Ile Ser Asp Thr Tyr Val Gly Arg Phe Lys Thr Ile Ala Phe
        115                 120                 125

Ala Ser Phe Ala Thr Leu Leu Gly Leu Ile Thr Ile Thr Leu Thr Ala
    130                 135                 140

Ser Phe Pro Gln Leu His Pro Ala Ser Cys Asn Ser Gln Asp Pro Leu
145                 150                 155                 160

Ser Cys Gly Gly Pro Asn Lys Leu Gln Ile Gly Val Leu Leu Leu Gly
                165                 170                 175

Leu Cys Phe Leu Ser Val Gly Ser Gly Gly Ile Arg Pro Cys Ser Ile
            180                 185                 190

Pro Phe Gly Val Asp Gln Phe Asp Gln Arg Thr Glu Glu Gly Val Lys
        195                 200                 205

Gly Val Ala Ser Phe Phe Asn Trp Tyr Tyr Met Thr Phe Thr Val Val
    210                 215                 220
```

Leu Ile Ile Thr Gln Thr Val Val Tyr Ile Gln Asp Gln Val Ser
225                 230                 235                 240

Trp Ile Ile Gly Phe Ser Ile Pro Thr Gly Leu Met Ala Leu Ala Val
            245                 250                 255

Val Met Phe Phe Ala Gly Met Lys Arg Tyr Val Tyr Val Lys Pro Glu
        260                 265                 270

Gly Ser Ile Phe Ser Gly Ile Ala Gln Val Ile Val Ala Ala Arg Lys
    275                 280                 285

Lys Arg Lys Leu Lys Leu Pro Ala Glu Asp Gly Thr Val Thr Tyr
290                 295                 300

Tyr Asp Pro Ala Ile Lys Ser Ser Val Leu Ser Lys Leu His Arg Ser
305                 310                 315                 320

Asn Gln Phe Arg Cys Leu Asp Lys Ala Ala Val Val Ile Glu Gly Asp
                325                 330                 335

Leu Thr Pro Glu Gly Pro Pro Ala Asp Lys Trp Arg Leu Cys Ser Val
            340                 345                 350

Gln Glu Val Glu Val Lys Cys Leu Ile Arg Ile Val Pro Ile Trp
            355                 360                 365

Ser Ala Gly Ile Ile Ser Leu Ala Ala Met Thr Thr Gln Gly Thr Phe
370                 375                 380

Thr Val Ser Gln Ala Leu Lys Met Asp Arg Asn Leu Gly Pro Lys Phe
385                 390                 395                 400

Glu Ile Pro Ala Gly Ser Leu Ser Val Ile Ser Leu Leu Thr Ile Gly
                405                 410                 415

Ile Phe Leu Pro Phe Tyr Asp Arg Val Phe Val Pro Phe Met Arg Arg
            420                 425                 430

Ile Thr Gly His Lys Ser Gly Ile Thr Leu Leu Gln Arg Ile Gly Thr
            435                 440                 445

Gly Ile Val Phe Ala Ile Phe Ser Met Ile Val Ala Gly Ile Val Glu
    450                 455                 460

Arg Met Arg Arg Ile Arg Ser Ile Asn Ala Gly Asp Pro Thr Gly Met
465                 470                 475                 480

Thr Pro Met Ser Val Phe Trp Leu Ser Pro Gln Leu Ile Leu Met Gly
            485                 490                 495

Leu Cys Glu Ala Phe Asn Ile Ile Gly Gln Ile Glu Phe Phe Asn Ser
            500                 505                 510

Gln Phe Pro Glu His Met Arg Ser Ile Ala Asn Ser Leu Phe Ser Leu
        515                 520                 525

Ser Phe Ala Gly Ser Ser Tyr Leu Ser Ser Phe Leu Val Thr Val Val
    530                 535                 540

His Lys Phe Ser Gly Gly His Asp Arg Pro Asp Trp Leu Asn Lys Asn
545                 550                 555                 560

Leu Asn Ala Gly Lys Leu Asp Tyr Phe Tyr Tyr Leu Ile Ala Val Leu
                565                 570                 575

Gly Val Val Asn Leu Val Tyr Phe Trp Tyr Cys Ala Arg Gly Tyr Arg
            580                 585                 590

Tyr Lys Val Gly Leu Pro Ile Glu Asp Phe Glu Glu Asp Lys Ser Ser
        595                 600                 605

Asp Asp Val Glu Met Thr Ser Lys Lys Ser Met Lys
610                 615                 620

<210> SEQ ID NO 5
<211> LENGTH: 232
<212> TYPE: DNA

```
<213> ORGANISM: Carnation etched ring virus

<400> SEQUENCE: 5
agcttgcatg cctgcaggtc gagcttttag gattccatag tgataagata tgttcttatc     60
taaacaaaaa agcagcgtcg gcaaaccata cagctgtcca caaaaaggaa aggctgtaat    120
aacaagcgga cccagcttct cagtggaaga tactttatca gacactgaat aatggatgga    180
ccctaccacg attaaagagg agcgtctgtc taaagtaaag tagagcgtct tt            232

<210> SEQ ID NO 6
<211> LENGTH: 54
<212> TYPE: DNA
<213> ORGANISM: Arabidopsis thaliana

<400> SEQUENCE: 6
ggggacaagt ttgtacaaaa aagcaggcty yatggagagc aaagggagtt ggac           54

<210> SEQ ID NO 7
<211> LENGTH: 54
<212> TYPE: DNA
<213> ORGANISM: Arabidopsis thaliana

<400> SEQUENCE: 7
ggggaccact ttgtacaaga aagctgggty tcagcagtct tcaactgaaa atcc           54

<210> SEQ ID NO 8
<211> LENGTH: 36
<212> TYPE: DNA
<213> ORGANISM: Arabidopsis thaliana

<400> SEQUENCE: 8
atcggtacca tggttttgga ggatagaaag gacggt                                36

<210> SEQ ID NO 9
<211> LENGTH: 36
<212> TYPE: DNA
<213> ORGANISM: Arabidopsis thaliana

<400> SEQUENCE: 9
agcgagctct catttcatcg atttcttcga agtcat                                36

<210> SEQ ID NO 10
<211> LENGTH: 19
<212> TYPE: DNA
<213> ORGANISM: Escherichia coli

<400> SEQUENCE: 10
gtgtaaaacg acggccagt                                                   19

<210> SEQ ID NO 11
<211> LENGTH: 19
<212> TYPE: DNA
<213> ORGANISM: Escherichia coli

<400> SEQUENCE: 11
aggaaacagc tatgaccat                                                   19
```